United States Patent
Niyikiza et al.

(10) Patent No.: US 12,115,256 B2
(45) Date of Patent: Oct. 15, 2024

(54) TARGETED LIPOSOMAL GEMCITABINE AND METHODS THEREOF

(71) Applicant: L.E.A.F. HOLDINGS GROUP LLC, Gulph Mills, PA (US)

(72) Inventors: Clet Niyikiza, Gulph Mills, PA (US); Victor Moyo, Ringoes, NJ (US); Zhenghong Xu, Arlington, MA (US); Kaniz Khalifa, Billericsa, MA (US)

(73) Assignee: L.E.A.F. HOLDINGS GROUP LLC, Gulph Mills, PA (US)

( * ) Notice: Subject to any disclaimer, the term of this patent is extended or adjusted under 35 U.S.C. 154(b) by 381 days.

(21) Appl. No.: 17/165,534

(22) Filed: Feb. 2, 2021

(65) Prior Publication Data

US 2021/0154140 A1    May 27, 2021

Related U.S. Application Data

(62) Division of application No. 15/587,018, filed on May 4, 2017, now Pat. No. 10,940,112.

(60) Provisional application No. 62/331,841, filed on May 4, 2016.

(51) Int. Cl.

| | | |
|---|---|---|
| A61K 9/127 | (2006.01) | |
| A61K 31/337 | (2006.01) | |
| A61K 31/4745 | (2006.01) | |
| A61K 31/555 | (2006.01) | |
| A61K 31/7068 | (2006.01) | |
| A61K 31/716 | (2006.01) | |
| A61K 33/243 | (2019.01) | |
| A61K 45/06 | (2006.01) | |
| A61K 47/68 | (2017.01) | |
| A61K 47/69 | (2017.01) | |
| A61P 31/18 | (2006.01) | |
| A61P 35/00 | (2006.01) | |
| C07K 16/28 | (2006.01) | |
| C07K 16/30 | (2006.01) | |

(52) U.S. Cl.
CPC .......... *A61K 9/1271* (2013.01); *A61K 31/337* (2013.01); *A61K 31/4745* (2013.01); *A61K 31/555* (2013.01); *A61K 31/7068* (2013.01); *A61K 33/243* (2019.01); *A61K 45/06* (2013.01); *A61K 47/6849* (2017.08); *A61K 47/6851* (2017.08); *A61K 47/6913* (2017.08); *A61P 31/18* (2018.01); *A61P 35/00* (2018.01); *C07K 16/28* (2013.01); *C07K 16/30* (2013.01); *C07K 2317/24* (2013.01); *C07K 2317/31* (2013.01); *C07K 2317/569* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,749,863 | B1 | 6/2004 | Chang et al. |
| 7,892,547 | B2 | 2/2011 | McBride et al. |
| 8,865,127 | B2 | 10/2014 | Chang et al. |
| 9,005,903 | B2 | 4/2015 | Rubin-Bejerano et al. |
| 2005/0002998 | A1 | 1/2005 | Chang et al. |
| 2005/0079184 | A1 | 4/2005 | Hsing-Chang et al. |
| 2007/0092558 | A1* | 4/2007 | Heavner ............... A61K 9/127 424/450 |
| 2008/0213183 | A1 | 9/2008 | Bally et al. |
| 2009/0053302 | A1 | 2/2009 | Boulikas |
| 2010/0279977 | A1 | 11/2010 | Belyakov et al. |
| 2011/0187012 | A1 | 8/2011 | Yoshimura et al. |
| 2011/0217363 | A1 | 9/2011 | Chen |
| 2012/0128587 | A1 | 5/2012 | Leamon et al. |
| 2012/0128667 | A1 | 5/2012 | Chow et al. |
| 2014/0099332 | A1 | 4/2014 | Testa et al. |
| 2014/0220116 | A1 | 8/2014 | Brahmbhatt et al. |
| 2014/0294896 | A1 | 10/2014 | Modi et al. |
| 2014/0356414 | A1* | 12/2014 | Wang ................... A61K 9/1271 514/44 A |
| 2016/0228573 | A1 | 8/2016 | Niyikiza et al. |
| 2016/0367481 | A1 | 12/2016 | Zale et al. |

FOREIGN PATENT DOCUMENTS

| | | |
|---|---|---|
| WO | WO 2015/013448 A1 | 1/2015 |
| WO | WO 2015/120112 A1 | 8/2015 |
| WO | WO 2016/025882 A2 | 2/2016 |

OTHER PUBLICATIONS

Pasut et al (Journal of Controlled Release, 2008, 127:239-248).*
Paolino et al (Journal of Controlled Release, 2010, 144-150).*
Varshochian et al (Clinical Lipidology, 2014, 9:571-585).*
Wibowo et al (PNAS, 2013, 110:15180-15188).*
Ledermann et al (Annals of Oncology, 2015, 26:2034-2043).*
Federico et al (International Journal of Nanomedicine, 2012, 7:5423-5436).*
Hood et al (Pharm. Res., 2013, 30:1597-1607).*
Kelly et al (Clinical Cancer Research, 2000, 6:3474-3479).*
Georgoulias et al (British Journal of Cancer, 2004, 91:482-488).*
Papa et al., "PEGylated liposomal Gemcitabine: insights into a potential breast cancer therapeutic", Cell Oncol. 36:449-457 (2013).
Pasut et al., "Antitumoral activity of PEG-gemcitabine prodrugs targeted by folic acid", Journal of Controlled Release, 127:239-248 (2008).
Ye et al., "Combination of gemcitabine-containing magnetoliposome and oxaliplatin-containing magnetoliposome in breast cancer treatment: A possible mechanism with potential for clinical application", Oncotarget, 7(28):43762-43778 (2016).
Gosselin et al., "Folate receptor-targeted liposomes as vectors for therapeutic agents", Biotechnology Annual Review, 8:103-131 (2002).
Li et al., "Self-assembled gemcitabine—gadolinium nanoparticles for magnetic resonance imaging and cancer therapy", Acta Biomater. 33:34-39 (2016).

(Continued)

*Primary Examiner* — Laura B Goddard
(74) *Attorney, Agent, or Firm* — Nixon & Vanderhye, PC

(57) ABSTRACT

This disclosure relates to a targeted PEGylated liposomal gemcitabine (PLG) composition comprising a PEGylated liposome encapsulating one or more agents comprising gemcitabine and a targeting moiety; pharmaceutical composition and methods comprising PLG or producing PLG; and manufacturing equipment for performing the methods.

24 Claims, 11 Drawing Sheets

(56) References Cited

OTHER PUBLICATIONS

Shi et al., "A current review of folate receptor alpha as a potential tumor target in non-small-cell lung cancer", Drug Design, Development and Therapy, 9:4989-4996 (2015).
Harasym et al., "Drug Ratio-Dependent Antagonism: A New Category of Multidrug Resistance and Strategies for Its Circumvention", Multidrug Resistance in Cancer, Methods in Molecular Biology, 596:291-323 (2010).
Kelemen, L.E., "The role of folate receptor a in cancer development, progression and treatment: Cause, consequences or innocent bystander?", Int. J. Cancer, 119: 243-250 (2006).
Zhao et al., "Determinants of the activities of antifolates delivered into cells by folate-receptor-mediated endocytosis", Cancer Chemotherapy and Pharmacology 75:1163-1173 (2015).
Gabizon et al., "Improved therapeutic activity of folate-targeted liposomal doxorubicin in folate receptor expressing tumor models", Cancer Chemotherapy and Pharmacology 66:43-52 (2010).
Lu et al., "Preclinical pharmacokinetics, tissue distribution, and antitumor activity of a folate-hapten conjugate-targeted immunotherapy in hapten-immunized mice", Mol. Cancer Ther., 5:3258-3267 (2006).
Bejerano et al., "Phagocytosis by Human Neutrophils Is Stimulated by a Unique Fungal Cell Wall Component", Cell Host Microbe, 2:55-67 (2007).
Saito, et al., "Distribution of Liposomes into Brain and Rat Brain Tumor Models by Convection-Enhanced Delivery Monitored with Magnetic Resonance Imaging", Cancer Research, 64:2572-2579 (2004).
Federico et al., "Gemcitabine-loaded Liposomes: Rationale, Potentialities and Future Perspectives", Internal Journal of Nanomedicine, 7:5423-5436 (2012).
Immordino et al., "Preparation, characterization, cytotoxicity and pharmacokinetics of liposomes containing lipophilic gemcitabine prodrugs", Journal of Controlled Release, 100:331-346 (2004).
Mamot et al., "Extensive distribution of liposomes in rodent brains and brain tumors following convection enhanced delivery", Journal of Neuro-Oncology, 68:1-9 (2004).
U.S. Appl. No. 62/037,597, filed Aug. 14, 2014; 48 pages.
A Communication forwarding the International Search Report mailed Sep. 14, 2017, in a corresponding International Application No. PCT/US17/31083 (20 pages).
Lehtinen et al., "Pre-Targeting and Direct Immunotargeting of Liposomal Drug Carriers to Ovarian Carcinoma," PLoS ONE, 7:e41410, internet pp. 1-10 (2012).
Ledermann et al., "Targeting the folate receptor: diagnostic and therapeutic approaches to personalize cancer treatments." Annals of Oncology 26 (10):2034-2043 (2015).
Li et al., "A novel application of maleimide for advanced drug delivery: in vitro and in vivo evaluation of maleimide-modified pH-sensitive liposomes," International Journal of Nanomedicine, 8:3855-3866 (2013).
Shmeeda et al., "Intracellular uptake and intracavitary targeting of folate-conjugated liposomes in a mouse lymphoma model with up-regulated folate receptors," Molecular Cancer Therapy, 5(4):818-824 (2006).
Zwicke et al., "Utilizing the folate receptor for active targeting of cancer nanotherapeutics," Nano Reviews, 3: 18496, internet pp. 1-11 (2012).
Tseng et al., "Translocation of Liposomes into Cancer Cells by Cell-Penetrating Peptides Penetratin and Tat: A Kinetic and Efficacy Study," Molecular Pharmacology, 62:864-872 (2002).
Pasut et al., "Antitumoral activity of PEG-gemcitabine prodrugs targeted by folic acid," Journal of Controlled Release, 127(3):239-248 2008).
Paolino et al., "Gemcitabine-loaded PEGylated unilamellar liposomes vs GEMZAR®: Biodistribution, pharmacokinetic features and in vivo antitumor activity," Journal of Controlled Release 144(2):144-150 (2010).
Varshochian et al., "Utilizing liposomes and lipid nanoparticles to overcome challenges in breast cancer treatment," Clinical Lipidology, 9(5):571-585 (2014).
Wibowo et al., "Structures of human folate receptors reveal biological trafficking states and diversity in folate and antifolate recognition," PNAS 110(38):15180-15188 (2013).
Tokunaka et al., "Application of Candida solubilized cell wall β-glucan in antitumor immunotherapy against P815 mastocytoma in mice," International Immunopharmacology, 2(1):59-67 (2002).
Kodama et al., "Can Maitake MD-Fraction Aid Cancer Patients?" Alternative Medicine Review 7(3):236-239 (2002).
Kelly et al., "A Phase I/II Trial of Paclitaxel, Carboplatin, and Gemcitabine in Untreated Patients with Advanced Non-Small Cell Lung Cancer," Clinical Cancer Research, 6(9):3474-3479 (2000).
Georgoulias et al., "Irinotecan plus gemcitabine vs irinotecan for the second-line treatment of patients with advanced non-small-cell lung cancer pretreated with docetaxel and cisplatin: a multicentre, randomised, phase II study," British Journal of Cancer, 91:482-488 (2004).
Hood et al., "Microfluidic Synthesis of PEG- and Folate— Conjugated Liposomes for One-Step Formation of Targeted Stealth Nanocarriers," Pharm. Res., 30:1597-1607 (2013).

* cited by examiner

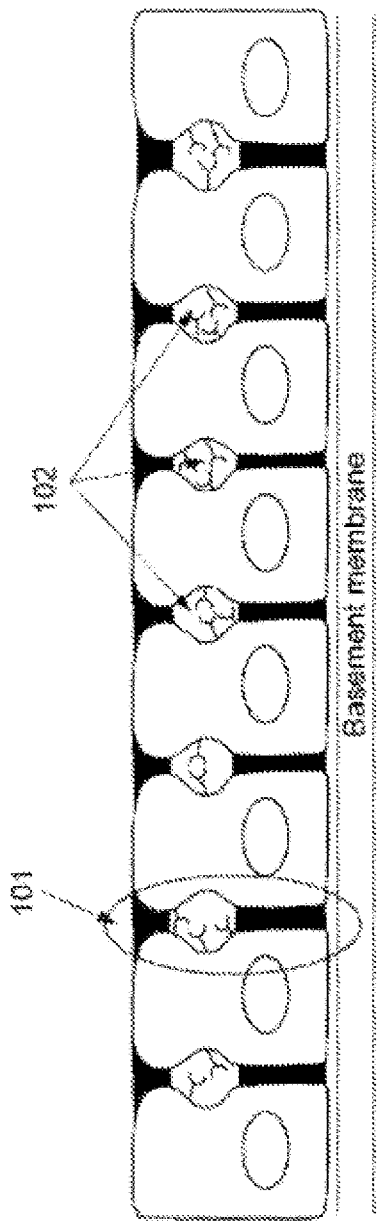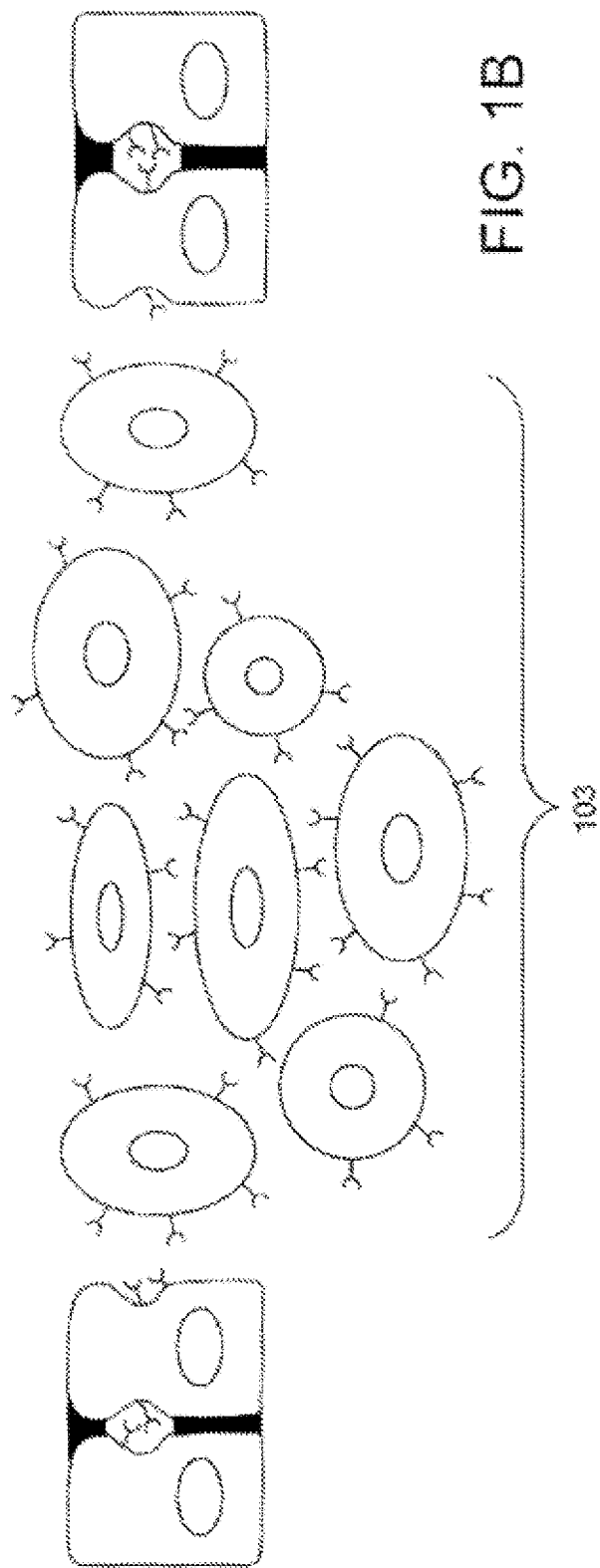

A
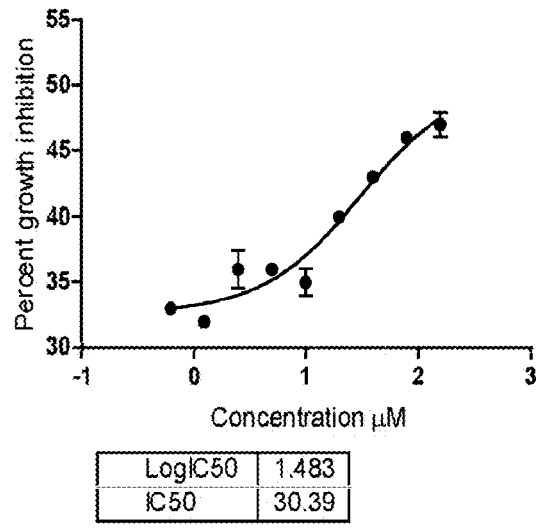
B
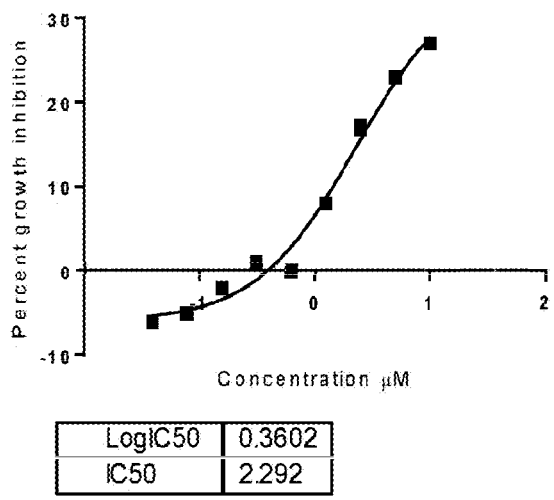
Figure 2

A
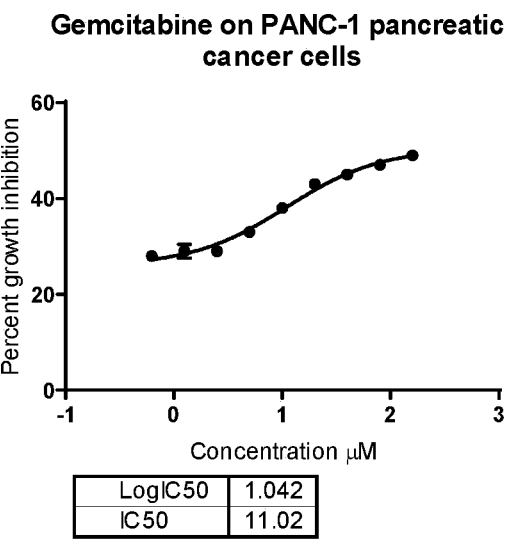
B
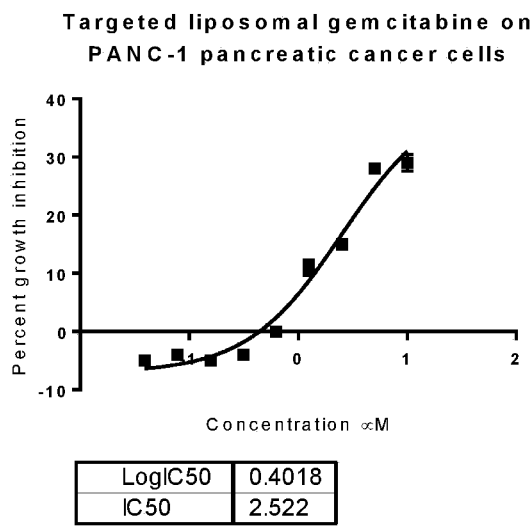
Figure 3

A
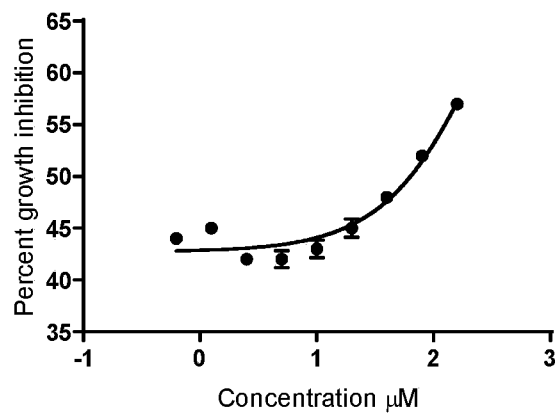
B
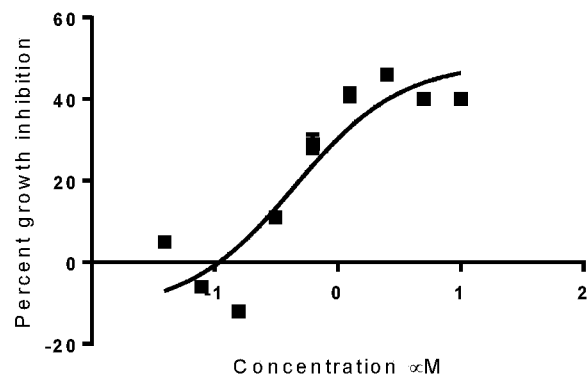
Figure 4

A
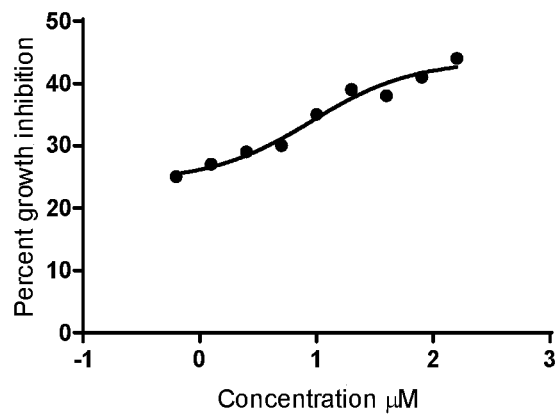
B
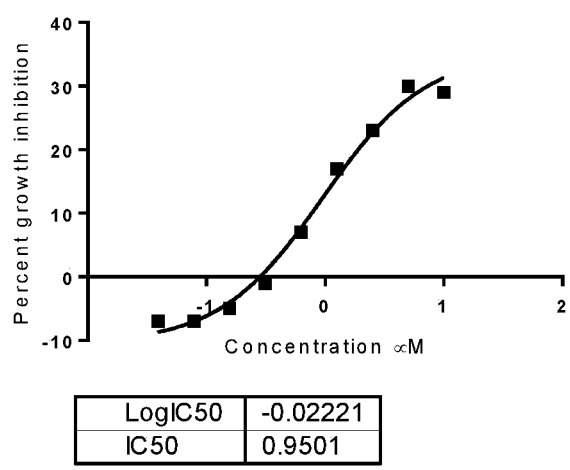
Figure 5

A  Negative control:
CD34+ cells without growth factors that promote neutrophil differentiation
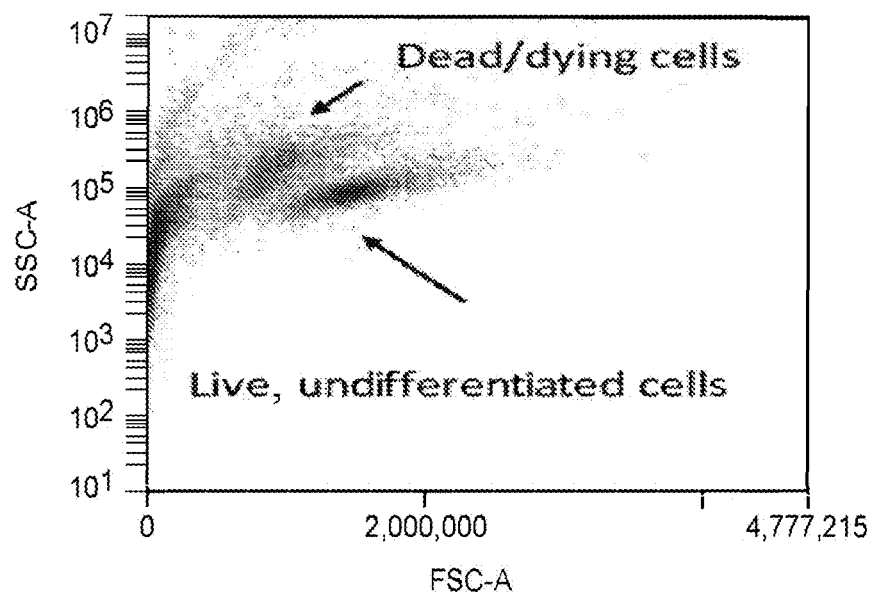
B  Positive control:
CD34+ cells without growth factors that promote neutrophil differentiation
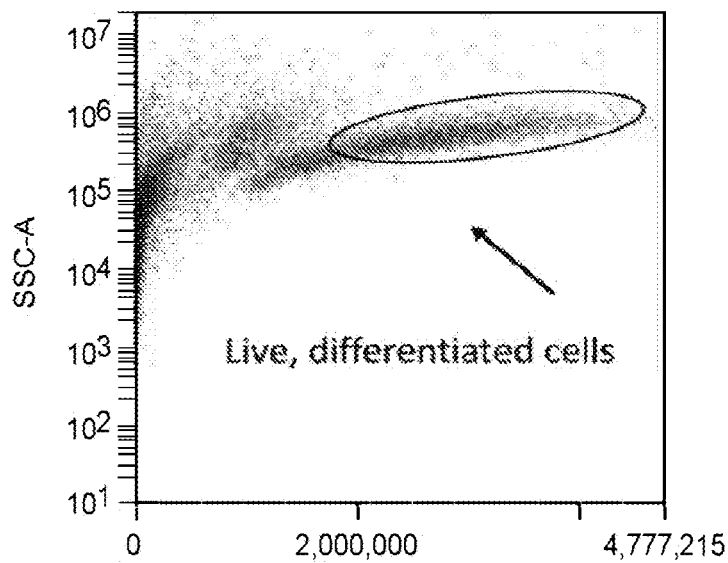
Figure 8

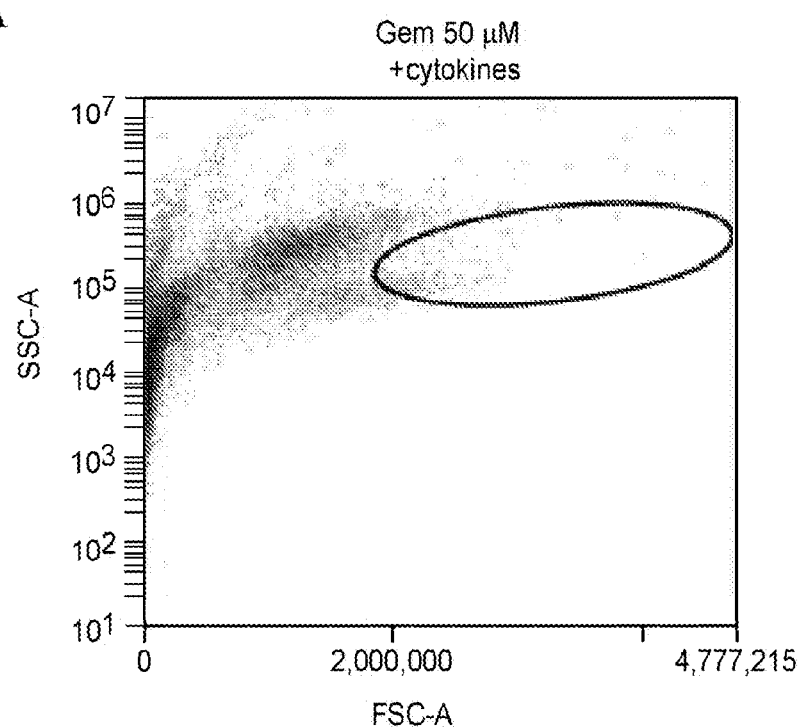
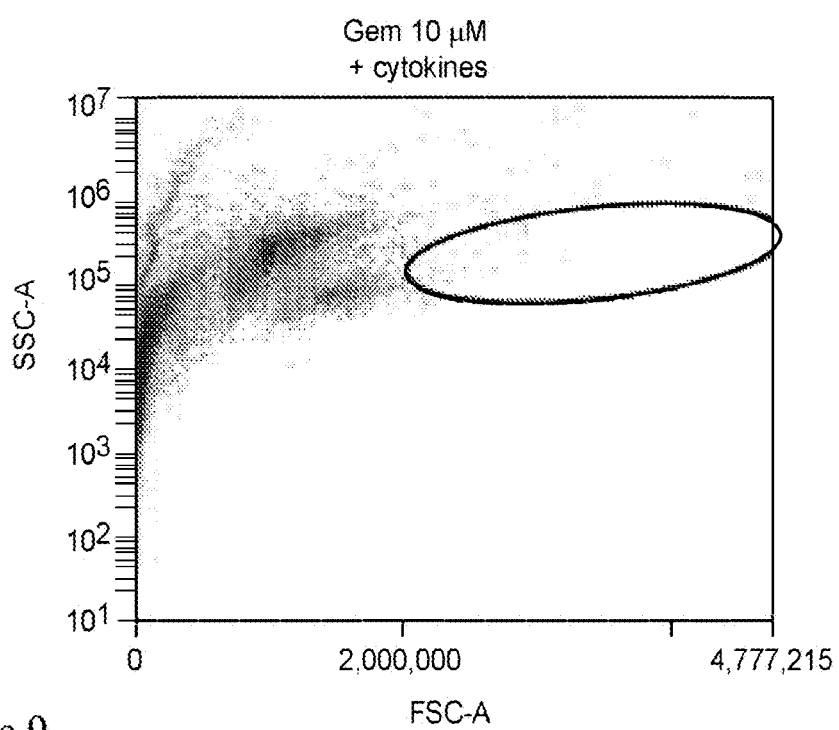
Figure 9

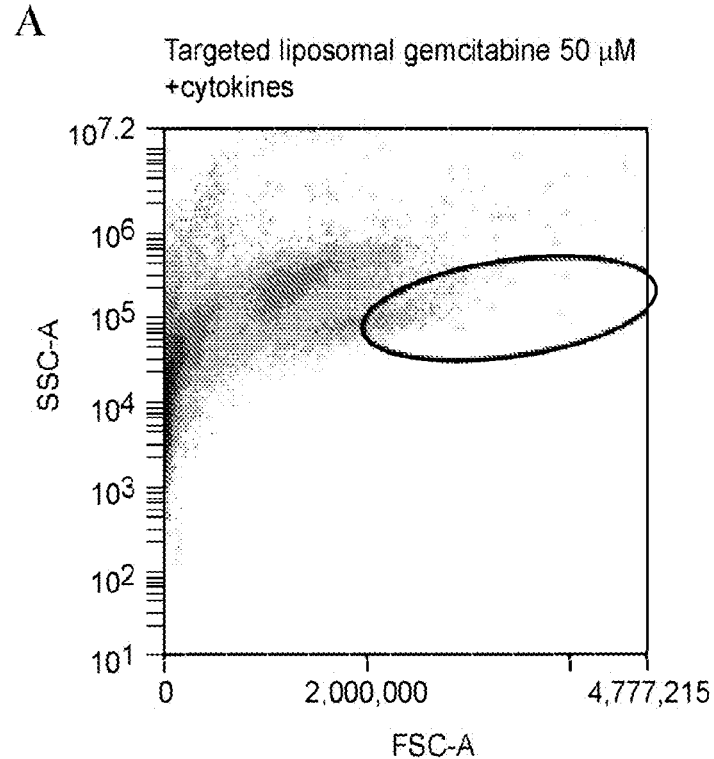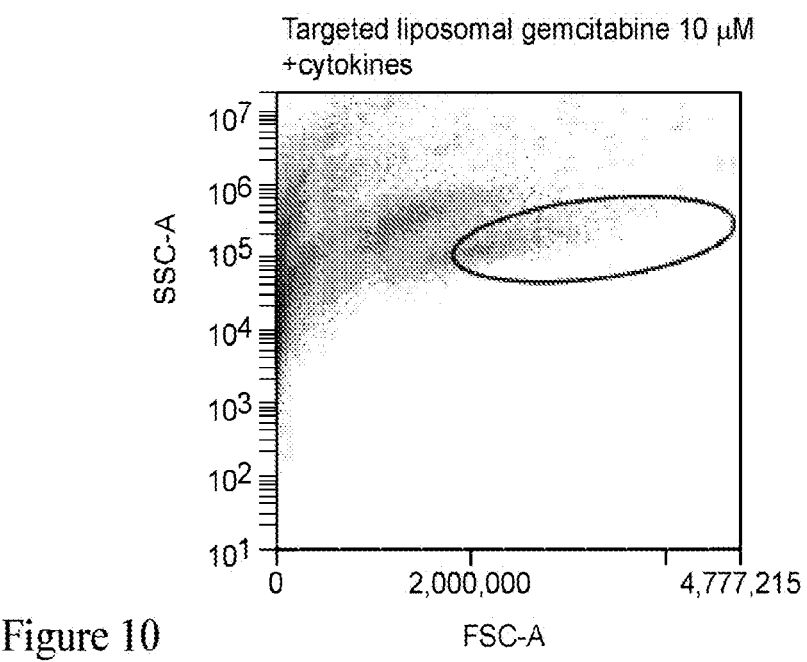
Figure 10

Reduction of toxicity on bone marrow production of neutrophils
A
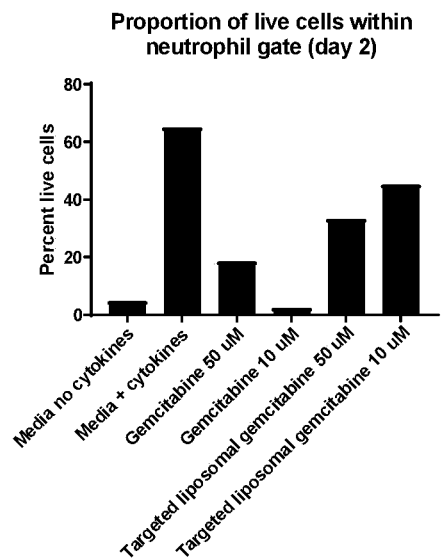
B
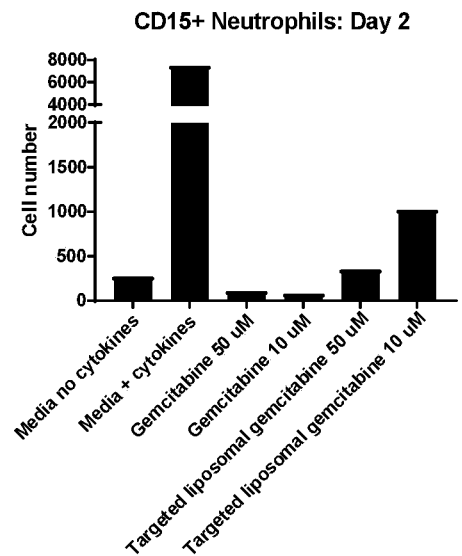
Figure 11

TARGETED LIPOSOMAL GEMCITABINE AND METHODS THEREOF

CROSS-REFERENCE TO RELATED APPLICATION

This application is a Divisional of U.S. application Ser. No. 15/587,018, filed on May 4, 2017, and claims priority under 35 U.S.C. § 119 to U.S. Provisional Patent application No. 62/331,841, filed on May 4, 2016 in the U.S. Patent and Trademark Office, the disclosure of which is incorporated by reference herein in its entirety.

BACKGROUND

Cancer is a very difficult disease to treat due to diversity of cancer type, mechanisms involved in disease progression and patient variability associated with underlying patient genetic make-up. Early forms of cancer treatment have primarily consisted of cytotoxic agents, including antineoplastic antimetabolites such as gemcitabine. Antimetabolites, including antifolates such as pemetrexed and lometrexol, fluoropyrimidines, such as 5FU or capecitabine, and nucleoside analogs, such as gemcitabine that masquerade as purine or pyrimidine which become the building blocks of DNA. They prevent purine or pyrimidine from becoming incorporated into DNA during the "S" phase (or DNA synthesis phase of the cell cycle), stopping normal development and division of a cell.

Gemcitabine, a member of the class of drugs known as nucleoside analogs, blocks an intracellular enzyme which converts the cytosine nucleotide into the deoxy derivative. In addition, DNA synthesis is further inhibited because gemcitabine blocks the incorporation of the thymidine nucleotide into the DNA strand.

Gemcitabine passes through the cell membrane with difficulty because its primary transport mechanism is passive diffusion. The gemcitabine transport mechanism requires active transporters. There are five nucleoside transporters that are involved in cell uptake of gemcitabine: two equilibrative sodium-dependent type (hENT1, hENT2) nucleoside transporters and three concentrative sodium-dependent nucleoside type (hCNT1, hCNT2, hCNT3) nucleoside transporters.

Gemcitabine exhibits cell phase specificity, primarily killing cells undergoing DNA synthesis (S-phase) and also blocking the progression of cells through the G1/S-phase boundary. Gemcitabine is metabolized intracellularly by nucleoside kinases, such as deoxycytidine kinase, to the active diphosphate (dFdCDP) and triphosphate (dFdCTP) nucleosides. The cytotoxic effect of gemcitabine is attributed to a combination of two actions of the diphosphate and the triphosphate nucleosides, which leads to inhibition of DNA synthesis. First, gemcitabine diphosphate inhibits ribonucleotide reductase, which is responsible for catalyzing the reactions that generate the deoxynucleoside triphosphates for DNA synthesis. Inhibition of this enzyme by the diphosphate nucleoside causes a reduction in the concentrations of deoxynucleotides, including dCTP. Second, gemcitabine triphosphate competes with dCTP for incorporation into DNA. The reduction in the intracellular concentration of dCTP (by the action of the diphosphate) enhances the incorporation of gemcitabine triphosphate into DNA, a phenomenon also referred to as "self-potentiation." After the gemcitabine nucleotide is incorporated into DNA, only one additional nucleotide is added to the growing DNA strands. After this addition, there is inhibition of further DNA synthesis. DNA polymerase epsilon is unable to remove the gemcitabine nucleotide and repair the growing DNA strands, a phenomenon also known as "masked chain termination."

Historically, antimetabolites such as gemcitabine have been broadly used in oncology, irrespective of disease stage or prior treatment (line of therapy). They remain an important treatment in many types of cancer including, but not limited to, pancreas, lung, ovarian, bladder and breast.

In the treatment of advanced pancreatic, breast, ovarian and bladder cancers, gemcitabine is approved for use with or without platinum or taxane anticancer agents. Gemcitabine is indicated for the treatment of advanced ovarian cancer that has relapsed at least 6 months after completion of platinum-based therapy; for the treatment of metastatic ovarian cancer; for the treatment of inoperable, locally advanced (Stage IIIA or IIIB), or metastatic (Stage IV) non-small cell lung cancer; and for the treatment of locally advanced (nonresectable Stage II or Stage III) or metastatic (Stage IV) adenocarcinoma of the pancreas. Gemcitabine is also indicated for the treatment of bladder cancer with regulatory approval outside the United States.

Preclinical toxicology studies conducted in mice, rats and dogs suggested early on that myelosuppression, also referred to as toxicity of the bone marrow, would be the major toxicity associated with gemcitabine therapies. Most importantly, these studies showed that the degree of toxicity encountered was directly linked to plasma levels of cytidine deaminase, the enzyme known to be primarily responsible for the breakdown, also referred to as deamination, of gemcitabine dFdC into its inactive metabolite 2', 2'-difluorodioxy-uridine (dFDU). Natural plasma levels of cytidine deaminase have been shown to vary by species. For example, plasma levels of cytidine deaminase have been shown to be low in rats but high in human plasma and in human liver. Furthermore, tumor associated macrophages (TAMs) found in the tumor microenvironment have been shown to secrete increased levels of cytidine deaminase. To reach the intracellular target ribonucleotide reductase, gemcitabine relies on the human equilibrative nucleoside transporter-1 (hENT1), the main enzyme responsible for transporting gemcitabine across cell membrane into the cell.

Gemcitabine remains to-date the backbone of many treatments for many cancers when given alone or given in combination with a member of other classes of anticancer agents, such as platinum (for example, cisplatin, carboplatin, oxaliplatin) or taxanes (for example, paclitaxel-TAXOL, docetaxel-TAXOTERE, cabazitaxel-JEVTANA®). However, the antitumor efficacy of gemcitabine based treatment regimen may be hindered by hypoxia.

Hypoxia, a condition in which the body or a region of the body is deprived of adequate oxygen supply, is either generalized affecting the whole body, or local affecting a region of the body. Hypoxia is a major underlying driver of many diseases; the top four leading causes of death, both in the US and globally; namely ischemic heart disease, stroke, COPD (chronic obstructive pulmonary disease) and lower respiratory tract infections are attributable to hypoxic phenomena. Hypoxia is also frequently encountered in traumatic and other states of shock. More relevant to the present context, hypoxia has been linked to cancer.

Tumor hypoxia, a situation where tumor cells have been deprived of oxygen, is a feature of advanced solid tumors. The commonly proposed explanation for this lack of oxygen is that as a tumor grows, it rapidly outgrows its blood supply, leaving portions of the tumor with regions where the oxygen concentration is significantly lower than in healthy tissues. Hypoxic microenvironments in solid tumors are a result of available oxygen being consumed within 70 to 150 μm of tumor vasculature by rapidly proliferating tumor cells thus limiting the amount of oxygen available to diffuse further into the tumor tissue. In order to support continuous growth and proliferation in challenging hypoxic environments, cancer cells are found to alter their metabolism. Hypoxia has been identified in cancer as a major contributor to poor prognosis and has also been linked to poor treatment outcome with chemotherapy and radiation-based treatment modalities. Data have shown that hypoxia promotes tumor progression as well as resistance to therapies, such as radiation and chemotherapy, including but not limited to anticancer platinum agents, such as cisplatin, carboplatin and oxaliplatin; and taxanes, such as paclitaxel and taxotere.

The antitumor efficacy of gemcitabine, given alone or given in combination with a platinum (for example cisplatin, carboplatin, oxaliplatin) or a taxane (for example paclitaxel, taxotere or cabazitaxel), is hindered by a number of hypoxia-related factors including, but not limited to:

Limited Gemcitabine Delivery to Intracellular Tumor Microenvironment

Gemcitabine passes through the cell membrane with difficulty because it is moved across by passive diffusion, but requires active transporters. There are five nucleoside transporters that are involved in its cell uptake: two equilibrative sodium-dependent type (hENT1, hENT2) nucleoside transporters and three concentrative sodium-dependent nucleoside type (hCNT1, hCNT2, hCNT3) nucleoside transporters, with hENT1 being the main gemcitabine transporter. Hypoxia has been associated with resistance to nucleoside analogs, such as gemcitabine, by decreasing the expression of the human cross-cell membrane equilibrative nucleoside transporters hENT1, hENT2 and concentrative nucleoside transporter hCNT3, thereby most likely decreasing transport of gemcitabine and other nucleoside analogues into tumor cells.

Gemcitabine Intratumor Cell Inhibition of Ribonucleotide Reductase Compromised

Hypoxia has been associated with a decrease in intracellular tumor ribonucleotide reductase, an enzyme required for the antitumor effect of gemcitabine. Indeed, this decrease leads to cell cycle arrest in G1 or G2 phase, thereby allowing DNA repair before progression to S or M phase.

Increased Breakdown of Gemcitabine

Cytidine Deaminase is the main enzyme responsible for the breakdown of gemcitabine 2', 2'-difluorodioxy-cytidine (dFdC), also referred to as gemcitabine deamination, into its inactive metabolite 2', 2'-difluorodioxy-uridine (dFDU). It has also been observed that under hypoxic conditions, intratumor cell levels of cytidine deaminase may be substantially increased by macrophages and monocytes in tumors and possible other disease states. In pancreatic cancer specifically, upregulation of cytidine deaminase by tumor associated macrophages has been linked to decreased gemcitabine cytotoxicity.

Taxanes Potentiate Gemcitabine by Decreasing Cytidine Deaminase

One of the ways taxanes, such paclitaxel or nab-paclitaxel, decrease cytidine deaminase has been observed to be through increasing reactive oxygen species (ROSs) which has been shown to deactivate cytidine deaminase. One of the strategies to decrease intratumoral gemcitabine breakdown by cytidine deaminase is to improve its antitumor effect by combining it with a taxane such as albumin-bound paclitaxel.

Antitumor Effect of Platinum Drugs Like Cisplatin Impaired by Hypoxia

Hypoxia-induced chemoresistance to cisplatin in tumor cells, such as non-small cell lung cancer (NSCLC) cells, is through the Hypoxia Inducible Factor-1 (HIF-1) pathway. The most common pathway of multidrug residtance-1 (MDR-1) regulation may not be involved in hypoxia-induced chemoresistance to cisplatin.

Antitumor Effect of Taxanes Like Paclitaxel Impaired by Hypoxia:

Hypoxia has been shown to impair the antitumor effect of paclitaxel, for example, in lung cancer cell lines via HIF-1. As another example, HIF-1alpha, stimulated by hypoxia, has been shown in ovarian cancer cell lines to exert a pivotal role in chemo-resistance by G0/G1 cell-cycle arrest. Eliminating hypoxic conditions or silencing HIF-1alpha by small interference RNA (siRNA) or avoiding hypoxia impact on treatment, might provide a potent tool to enhance paclitaxel effectiveness in treatment of human ovarian cancer.

Taken together, these hypoxia-related factors above show how tumor hypoxia enhances the inability for gemcitabine, whether given alone or given in combination with a platinum anticancer drug like cisplatin or a taxane like paclitaxel, to overcome the pharmacological obstacles posed by increased levels of cytidine deaminase encountered as gemcitabine makes its way through plasma and tumor microenvironment to penetrate tumor cell and exert its effect on the tumor cell microenvironment target. In addition to the impairment by hypoxia of gemcitabine based treatment antitumor effect when given alone or given in combination with a platinum anticancer drug like cisplatin or a taxane like paclitaxel, gemcitabine combination treatment with a taxane or with a platinum agent has been associated with severe hematologic and nonhematologic toxic effects for patients.

The clinical efficacy of gemcitabine given alone or given in combination with cisplatin or with paclitaxel in the treatment of the various human cancers has been demonstrated with a series of clinical studies conducted across multiple countries at various stages of its early and late-stage development. These studies also highlighted the major drawback of gemcitabine based treatment when serious and in some cases life-threatening myelosuppressive and non-hematologic toxicities rates were observed with gemcitabine based treatments. Myelosuppression, together with severe nausea and vomiting, have been observed to be the core primary reason patients discontinue gemcitabine-based therapy, hindering the ability to deliver efficacious treatment. Significant pharmacological obstacles remain in place and continue to hinder the ability to optimize clinical efficacy and to reduce and/or minimize toxicity in patients treated with gemcitabine based therapy.

SUMMARY

This disclosure is directed to various embodiments for compositions, methods, and manufacturing equipment for treating diseases and disorders including cancers, tumors, and neoplastic diseases.

One example embodiment is directed to a targeted PEGylated liposomal gemcitabine (PLG) composition, comprising: a PEGylated liposome encapsulating one or more agents, wherein the one or more agents comprises gemcitabine; and one or more targeting moiety comprising an amino acid chain, the amino acid chain comprising a plurality of amino acids, at least one of the one or more targeting moiety having a specific affinity for at least one type of folate receptor, the one or more targeting moiety attached to one or both of a PEG and an exterior of the liposome. The specific affinity may include an equilibrium dissociation constant (Kd) in a range of $0.5 \times 10^{-10}$ to $10 \times 10^{-6}$ moles [0.05 nanoMole to 10 μMole] for at least one type of folate receptor. Further, the specific affinity may be an average affinity for the targeting moiety.

The PLG composition comprises a PEGylated lipoome. The PEGylated liposome encapsulates, or contains within the liposome, one or more agents. The one or more agent may be gemcitabine. At least the exterior of the PEGylated liposome comprises one or more targeting moiety which can be a peptide or a protein that binds a folate receptor. In an example embodiment, the binding is to the non-ligand-binding part of the folate receptor. In another example embodiment, the binding is to the ligand binding part of the folate receptor.

The one or more targeting moiety may be one or more targeting moieties with each targeting moiety having the same or similar binding specificity or different binding specificity. The one or more targeting moiety may comprise, for example, 1, 2, 3, 4, 5 or more targeting moieties. For example, each targeting moiety may comprise a plurality of members. For another example, one targeting moiety may comprise a population of monoclonal antibodies.

The one or more targeting moiety may comprise, for example, a protein with one or more subunits, such as a heavy chain and light chain, comprising an antibody. In another example embodiment, at least one of the one or more targeting moiety may be a fragment of an antibody or a component of an antibody. The antibodies may be monospefic (binding to only one epitope), bispecific (binding to two epitopes that are different), or multispecific (binding to more than two epitopes such as three or four epitope which are each different). A multispecific antibody is possible, for example, if it is a multimeric antibody comprising two, three, four, or five or more epitope binding sites.

In an example embodiment, the PEGylated liposome may further comprising one or more of (1) an immunostimulatory agent, (2) a detectable marker and (3) a maleimide. Each of these may be attached and associated with the PEGylated liposome and may be disposed on at least one of the PEG and on the exterior of the liposome. For example, each of these components may be attached via covalent bond(s) to a PEG molecule or a component of the liposome.

In an example embodiment, the PEGylated liposome is an anionic liposome or a neutral liposome.

In an example embodiment, at least one of the one or more targeting moiety has the specific affinity for one or more selected from the group consisting of folate receptor alpha, folate receptor beta and folate receptor delta. For example, at least one of the one or more targeting moiety may have specific affinity to just one of folate receptor alpha, folate receptor beta and folate receptor delta. As another example, at least one of the one or more targeting moiety may have specific affinity to just folate receptor alpha and folate receptor beta.

In another example embodiment, at least one of the one or more targeting moiety may have the specific affinity for an epitope on a tumor cell surface antigen that is present on a tumor cell but absent or inaccessible on a non-tumor cell. For example, the epitope may be a cell surface marker associated with tumors and cancer cells. The epitope may be a cell surface marker that is always present in cells but only detectable in a cell that is transformed into a cancer or tumor cell. It is understood that the PEGylated liposome may comprise one or more targeting moieties. Where the tumor cell surface antigen is a receptor, the epitope may be the ligand binding site, or, alternatively, the epitope may be a part of the receptor not involved in ligand binding. The receptor may be, for example, one or more selected from the group consisting of: folate receptor alpha, folate receptor beta, and folate receptor delta.

In another example embodiment, the one or more targeting moiety may comprise, or may be, one or more selected from the group consisting of: an antibody, a humanized antibody, an antigen binding fragment of an antibody, a single chain antibody, a single-domain antibody, a monospecific antibody, a bi-specific antibody, a synthetic antibody, a pegylated antibody, and a multimeric antibody.

Encapsulation capacity is defined as the amount of drug that is ultimately entrapped in the liposome expressed as a fraction (percentage) of the amount of total lipid content used to make the liposomes. It is usually shown as Drug/Lipid ratio (g/mol or % (w/w). In an example embodiment the targeted PLG composition comprises an encapsulation capacity of at least 5% (w/w phosphate lipid) or a drug (gemcitabine)/lipid ratio of 60 g/mol. That is, at least 5% (w/wphosphate lipid; 7.7% to be precise) of the total weight of the targeted PLG composition is comprised of gemcitabine.

Encapsulation (Trapping) efficiency is the amount of drug (in this case gemcitabine) that ends up in the liposome/the total amount of drug (gemcitabine) used at the beginning to make the liposome. It is usually expressed as a percentage. In an example embodiment the targeted PLG composition comprises at least 10% (12% to be precise) of gemcitabine by weight entrapped entrapped. That is, at least 10% of the original quantity of gemcitabine used to make the liposomes was ultimately entrapped in liposomes during the process of formulation.

The PEGylated liposome, in any of the embodiments of the disclosure, may have a diameter in the range of 20 nm to 200 nm. In another embodiment, the PEGylated liposome may have a diameter of between 80 nm to 130 nm.

In an example embodiment, the targeted PLG composition is free of any reagent, chemical or protein that can degrade gemcitabine. These would include at least cytidine deaminase. In another example embodiment, the environment inside the PEGylated liposome is free of any reagent, chemical or protein that can degrade gemcitabine such as, for example, cytidine deaminase. Cytidine deaminase is one or more of the enzymes that converts gemcitabine and other nucleotide analogues into inactive forms in patient plasma, produced in tumor microenvironment by TAMs, and/or associated with hypoxic tumor microenvironment.

In an example embodiment, the PEGylated liposome encapsulates only one agent. The one agent may be gemcitabine. In another example embodiment, the PEGylated liposome comprises more than one agent. In this case, the one or more agents can be, at least one or more of platinum; platinum derivative; taxane; taxane derivative; camptothecin; and camptothecin derivative. The platinum derivative may be one or more of cisplatin, carboplatin and oxaliplatin. The taxane derivative may be one or more of paclitaxel, taxotere and cabazitaxel. The camptothecin derivative may be one or more of irinotecan, SN-38, and CPT-11. For example, the PEGylated liposome may encapsulate gemcitabine; gemcitabine and a platinum or platinum derivative; gemcitabine and a taxane or taxane derivative; gemcitabine and a camptothecin or camptothecin derivative; gemcitabine, a platinum or platinum derivative, a taxane or taxane derivative and a camptothecin or camptothecin derivative; or any combination or sub-combination above.

In one example embodiment, the targeted PEGylated liposomal gemcitabine (PLG) of this disclosure, when administered to a patient, results in a specific molar ratio of in the tumor micro-environment in a range of about 16:1 to about 1:64, or about 1:2. This specific molar ratio may refer to any one of a ratio of the following: (a) gemcitabine to platinum; (b) gemcitabine to platinum derivative; (c) gemcitabine to taxane; (d) gemcitabine to taxane derivative; (e) gemcitabine to camptothecin; (f) gemcitabine to camptothecin derivative.

In another example embodiment, the targeted PEGylated liposomal gemcitabine (PLG) of this disclosure comprises the various agents in a range of about 16:1 to about 1:64, or about 1:2. This specific molar ratio may refer to any one of a ratio of the following: (a) gemcitabine to platinum; (b) gemcitabine to platinum derivative; (c) gemcitabine to taxane; (d) gemcitabine to taxane derivative; (e) gemcitabine to camptothecin; (0 gemcitabine to camptothecin derivative.

In an example embodiment, the targeted PEGylated liposomal gemcitabine (PLG) composition may be such that when it is administered, it results in a molar ratio of [gemcitabine] to [platinum or platinum derivative] to [taxane or taxane derivative] to [camptothecin or camptothecin derivative] in the tumor micro-environment in a range of about 16:1:1:1 to about 1:64:64:64 or with a ratio of about 1:2:2:2. In another example embodiment, the targeted PEGylated liposomal gemcitabine (PLG) composition may be such that it comprises agents in a molar ratio of [gemcitabine] to [platinum or platinum derivative] to [taxane or taxane derivative] to [camptothecin or camptothecin derivative] in the tumor micro-environment in a range of about 16:1:1:1 to about 1:64:64:64 or with a ratio of about 1:2:2:2.

Another example embodiment is directed to a targeted PEGylated liposomal gemcitabine (PLG) composition wherein said PEGylated liposome further comprising one or more selected from the group consisting of a hapten and an antigen. The hapten may be, for example, one or more selected from the group consisting of fluorescein and Beta 1, 6-glucan.

Another example embodiment is directed to a pharmaceutical composition comprising the targeted PEGylated liposomal gemcitabine (PLG) as described in this disclosure.

Methods of using any of the targeted PEGylated liposomal gemcitabine described in this disclosure are also envisioned. The methods may involve delivering gemcitabine to a tumor expressing a folate receptor on its surface with the following steps: administering the targeted PLG composition as described in this disclosure in an amount to deliver a therapeutically effective dose of the gemcitabine to the tumor. The tumor may be in vivo in a subject or in vitro in culture. The subject may be, for example, a human or a nonhuman mammal, for example. Administration of the targeted PEGylated liposomal gemcitabine described in this disclosure may involve any method known for administration of pharmaceutical compositions. For example, such methods, wherein the tumor is in a subject, may involve administrating using a method selected from the group consisting of: infusion; injection; parenteral administration; topical administration; intraperitoneal injection; direct intra-tumor injection; intra-arterial injection; intravenous injection; subcutaneous injection; intramuscular injection; transcutaneous delivery; and intranasal delivery.

An example embodiment is directed to a method for treating cancer in a patient comprising administering to the patient an effective amount of the targeted PEGylated liposomal gemcitabine (PLG) composition as described. The cancer may be, for example, a tumor. The tumor may be a gemcitabine sensitive tumor such as, a tumor susceptible to treatment by gemcitabine alone (sensitive to gemcitabine as a monotherapy)—a gemcitabine monotherapy susceptible tumor. As an example, the tumor may be a tumor displaying a loss of apical-basal polarity.

The methods disclosed may inhibit or reduce tumor cell proliferation. An example embodiment is directed to a method of reducing a sign or symptom of cancer by administering to the patient an effective amount of the targeted PEGylated liposomal gemcitabine (PLG) composition as described so that the signs or symptoms of cancer are reduced or eliminated. The cancer that can be treated includes, at least, one or more selected from the group consisting of: pancreatic cancer; breast cancer; ovarian cancer; bladder cancer; lung cancer; mesothelioma, prostate cancer; head cancer; neck cancer; gastric cancer; gastrointestinal cancer; colon cancer; esophageal cancer; cervical cancer; kidney cancer; biliary duct cancer; gallbladder; hematologic malignancy; leukemia; and lymphoma.

Another example embodiment is directed to a method for treating human immunodeficiency virus (HIV) in a patient comprising administering to the patient an effective amount of the targeted PEGylated liposomal gemcitabine (PLG) composition according to this disclosure.

Methods of preparing the targeted PLG composition are also envisioned. For example, a method of preparing a targeted PLG composition of this disclosure may comprise the steps of: forming a mixture comprising liposomal components and one or more agents in solution; homogenizing the mixture to form liposomes in the solution; processing the mixture to form liposomes entrapping and/or encapsulating gemcitabine; and providing the one or more targeting moiety on a surface of the liposomes entrapping and/or encapsulating said one or more agents; the one or more targeting moiety having the specific affinity for at least one of folate receptor alpha, folate receptor beta and folate receptor delta. In the method, the processing step comprises one or more substeps selected from the group consisting of: thin film hydration; extrusion; in-line mixing; stirring; extrusion; and sonication.

Manufacturing equipment configured to perform the method is also envisioned. For example, the manufacturing equipment may comprise a programmed computer. Also, the manufacturing equipment may comprise a first apparatus for forming the mixture, homogenizing the mixture, and processing the mixture and a second apparatus for providing the one or more targeting moiety. In this case, the manufacturing equipment may comprise a computer for controlling the first and second apparatuses.

BRIEF DESCRIPTION OF THE DRAWINGS

The above and/or other aspects, features and attendant advantages of the present disclosure will become more apparent and readily appreciated from the following detailed description, taken in conjunction with the accompanying drawings, in which like reference numerals refer to like elements, and wherein:

FIG. 1A is a schematic illustrating normal tissue.

FIG. 1B is a schematic illustrating cancerous tissue.

FIG. 2 (A) depicts percent growth inhibition of gemcitabine on NCI-H2452 lung (mesothelioma) cancer cells; (B) depicts percent growth inhibition of Targeted Liposomal Gemcitabine on NCI-H2452 lung cancer cells.

FIG. 3 (A) depicts percent growth inhibition of gemcitabine on PANC-1 pancreatic cancer cells; (B) depicts percent growth inhibition of Targeted Liposomal Gemcitabine on PANC-1 pancreatic cancer cells.

FIG. 4 (A) depicts percent growth inhibition of gemcitabine on SKBR3 breast cancer cells; (B) depicts percent growth inhibition of Targeted Liposomal Gemcitabine on SKBR3 breast cancer cells.

FIG. 5 (A) depicts percent growth inhibition of gemcitabine on HPAF-II pancreatic cancer cells; (B) depicts percent growth inhibition of Targeted Liposomal Gemcitabine on HPAF-II pancreatic cancer cells.

FIG. 8 is a flow cytometry histogram of a neutrophil cell population (A) which has received no cytokines treatment and (B) which has received cytokine treatment.

FIG. 9 is a flow cytometry histogram of a neutrophil cell population (A) that has received cytokines treatment and 50 μM gemcitabine (B) that has received cytokines treatment and 10 μM gemcitabine.

FIG. 10 is a flow cytometry histogram of a neutrophil cell population (A) that has received cytokines treatment and 50 μM Targeted Liposomal Gemcitabine (B) that has received cytokines treatment and 10 μM Targeted Liposomal Gemcitabine.

FIG. 11 (A) is a bar chart showing the proportion of live cells within the neutrophil gate on day 2; and (B) is a bar chart showing the number of live cells within the neutrophil gate, using CD15+ as a marker, on day 2.

DETAILED DESCRIPTION

Figure 6:
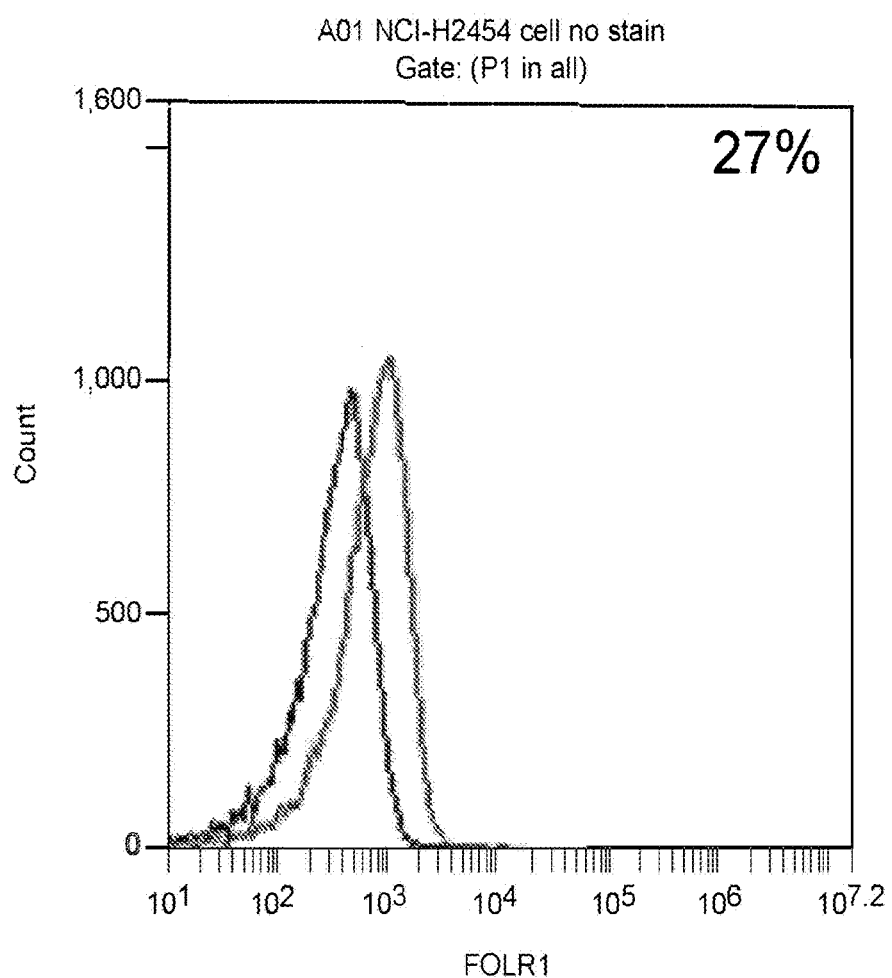
FIG. 6 is a flow cytometry histogram of a cell population showing that 27% of the cells exhibit high levels of folate receptor alpha on cancer cells.

The antitumor effect of gemcitabine and other nucleoside analogs depends on their ability to overcome the pharmacological obstacles encountered as they make their way through plasma and tumor microenvironment to penetrate tumor cell and exert their effect on their tumor cell microenvironment target.

In clinical practice, gemcitabine is approved and used in combination with a cytotoxic agent such as cisplatin in lung cancer, with carboplatin in ovarian cancer and with paclitaxel in pancreatic and breast cancers. Although these gemcitabine-based combination therapies have been found to be superior to monotherapy of each component drug, recent pre-clinical studies have shown that use of appropriate molar ratios of the combined drugs could result in synergistic cytotoxic effects while other molar ratios often result in antagonistic effects of the combination at the tumor cell level. Taken together, these observations suggest that it is critical to deliver the combined cytotoxic agents at synergistic/additive molar ratios inside the tumor cell (Harasym et al. Chapter 13 "Drug Ratio-Dependent Antagonism: A New Category of Multidrug Resistance and Strategies for Its Circumvention, in J. Zhou (ed.); Multidrug Resistance in Cancer, Methods in Molecular Biology, vol. 596 DOI 10.1007/978-1-60761-416-6_13 ©Humana Press), incorporated by reference herein in its entirety.

Because the primary reason that patients discontinue gemcitabine-based therapies is myelosuppression coupled with severe nausea and vomiting, the antitumor effectiveness of gemcitabine-based therapy depends on the ability to deliver a drug payload to the tumor cells that increases tumor cell killing while decreasing exposure of the gemcitabine based drug cocktail to normal cells.

A strategy to overcome these pharmacological challenges is to design a new chemical entity containing gemcitabine alone or gemcitabine in combination with one or more additional agents selected from (1) platinum, (2) platinum derivative, (3) taxane, (4) taxane derivative, (5) camptothecin, and (6) camptothecin derivative, as active agent(s) that may address one or more of the following objectives: First, shield gemcitabine from breakdown into its inactive metabolite dFdU by the high levels of cytidine deaminase found in patient plasma or produced in tumor microenvironment by TAMs or associated with hypoxic tumor microenvironment. Second, optimally deliver the drug payload of gemcitabine with or without the one or more additional agents to the tumor cells that maximizes and/or improves tumor cell killing while minimizing and/or reducing the pharmacological challenges for the drug payload to reach the tumor cells. Third, preferentially target tumor cells for exposure to gemcitabine-based drug payload and reduce and/or minimize exposure of normal cells, especially the high turnover normal cells in the bone marrow and in the epithelial lining of the gastrointestinal tract. Fourth, transport gemcitabine across cell membrane into a tumor cell in a manner that is primarily independent from the human cross-cell membrane nucleoside transporters typically associated with the gemcitabine transport mechanisms, including but not limited to the equilibrative nucleoside transporter hENT1. Fifth, deliver the combined cytotoxic agents at synergistic/additive, as opposed to antagonistic, molar ratios inside the tumor cell. Sixth, enhance cancer cell-directed immunotoxicity and immunosurveillance.

The new chemical entity is designed by carefully leveraging pharmacological understanding of cell and molecular biology pertaining to folate pathways. Specifically, this is achieved by exploiting differential cell polarity as well as folate receptor expression profile between tumor and normal tissue. This tumor tissue specific profile has been underappreciated as a strategy to safely deliver to tumor cells a drug payload that maximizes tumor cell killing while minimizing exposure of normal cells.

Folate uptake by normal cells or cancer cells is primarily mediated by reduced folate carriers (RFCs), but has also been shown to be mediated by proton-coupled folate transporter (PCFT). RFCs are an abundant cross-membrane transporter with low affinity for folates relative to folate receptor alpha (See Table I below). However, in advanced cancer folate transport is also mediated via folate receptors, such as, for example, and without limitation, FR-α. Because cancer cells are fast growing cells with a high demand for DNA precursors in the form of folates, they are susceptible to the effects of cytotoxic antimetabolites such as gemcitabine. However, fast growing normal cells, such as cells that line the gastrointestinal (GI) tract and cells of the bone marrow such as neutrophils, divide rapidly. Normal cells are therefore also susceptible to cytotoxic agents. Because of this, treatment with cytotoxic therapies has the potential to result in a collateral effect of killing fast-growing normal cells, thereby causing chemotherapy-related toxicities. The net result of these two clinical dynamics is that bone marrow and gastrointestinal (GI) tract cells have been the most prevalent sites of patients' life-threatening related toxicities. Some of the common toxicities have included mucositis, diarrhea, anemia, neutropenia, thrombocytopenia, and low white blood counts associated with immune-suppression, among others.

TABLE I

KELEMEN COMPARISON OF FOLATE RECEPTOR α
(FRα) AND REDUCED FOLATE CARRIER (RFC)
UPTAKE OF FOLATES

| Characteristic | FRα | RFC |
|---|---|---|
| Distribution | Restricted | Nearly all cells |
| Preferred substrate | Folic Acid | 5-mTHF[1] |
| Other substrates | 5-mTHF[1], antifolates to a lesser extent | Does not bind folic acid |
| Substrate binding concentration | Physiologic (nM) | Pharmacologic (μM) |
| Preferred substrate plasma levels | Low, unless folic acid intake >300 μg | Main circulating form |
| Binding affinity for folic acid | High: FRα binds folic acid ~ 10 times that of reduced folates $K_d$: < 1 nM[21,111] | Low: folic acid binds FRα 100-200 times greater than it binds RFC $K_m$: 200-400 μM[21] |
| Binding affinity for 5-mTHF and other reduced folates | High: $K_d$: 1-10 nM[21] | High: $K_m$: 1-10 μM[21] |
| Binding affinity for methotrexate | Low: $K_d$: >100 nM[21] | High: $K_m$: 1-5 μM[111] |

[1]5-methyltetrahydrofolate.

From Kelemen, L. E. The role of Folate receptor a in cancer development, progression and treatment: Cause, consequences or innocent bystander? Int. J. Cancer; 119. 243-250 (2006), the entire contents of which are incorporated herein by reference.

Many advanced cancers express folate receptors, such as, for example, and without limitation, folate receptor alpha (FR-α) and PCFTs. Folate receptors will be discussed herein with reference to FR-α for ease of description. However, it will be understood that other folate receptors may also be available for use in drug delivery in accordance with the present disclosure. Prior efforts to selectively deliver anticancer agents to cancer cells have focused on using folate pathways to deliver a toxic anticancer agent, with primary focus on FR-α because one of these pathways involves folate FR-α. These prior efforts were driven by three observations in cancer biology. First, FR-α is highly expressed by cancer cells relative to normal cells. Second, cancer cells preferentially express FR-α in order to efficiently uptake folates for the sustainment of their fast replication and proliferation needs. Third, as cancer progresses, FR-α is increasingly expressed by tumor cells.

Because of its high affinity to FR-α as noted in Table I above, folic acid was conventionally investigated as the targeting moiety with the intent to preferentially deliver a cytotoxic drug to cancer cells, either conjugated to a liposome containing the cytotoxic drug, or conjugated to the cytotoxic drug itself. This approach has not led to improved safety or efficacy in large part because it failed to recognize a key biological difference in exploiting folate pathways as an approach to deliver a cytotoxic to cancer cells while reducing and/or minimizing exposure of normal cells to the cytotoxic drug; with folic acid as the targeting ligand, normal cells were not being spared from toxicity since such a targeted drug payload can still be up taken by normal cells via RFCs or PCFTs. In other words, conventional targeting moieties seeking to exploit folate pathways, e.g., folic acid, are non-specific. Non-specific targeting moieties do not discriminate between normal and cancerous cells. In this regard, a targeted cytotoxic drug using folic acid as the targeting moiety is biologically no different than a regular untargeted cytotoxic because a drug of such construct binds to both folate receptor alpha and RFCs just like any other "folate-look alike" molecule that is indiscriminately uptaken by both cancer and normal cells.

Attempts have been made recently to develop PEGylated liposomal gemcitabine (PLG) with some limited success, but no attempt has been made to target PLG to a folate receptor or to specifically target FR-α with a targeting moiety that has a specific binding affinity to FR-α, and not to RFCs.

Using folic acid to target a liposome containing a cytotoxic agent has been attempted with no significant improvement over untargeted liposome (see discussion above). As a result, experts have suggested that trying to exploit folate receptor as a means for selective targeting of cancer cell may be ineffective and teaching away from the solutions set forth in the present disclosure. In fact, for example, investigators have opined that FR-α is unlikely to contribute to pharmacological activity (see, e.g., Zhao, Visentin and Goldman, "Determinants of the activities of antifolates delivered into cells by folate-receptor-mediated endocytosis," Cancer Chemotherapy and Pharmacology (2015)). More importantly, investigators researching folate-targeted PEGylated liposomal doxorubicin (a popular anthracycline anticancer drug) have concluded that folate targeting confers only a modest therapeutic improvement to PLD and that the potential clinical value of this approach has yet to be determined (see, e.g., Zalipsky et al. "Improved therapeutic activity of folate-targeted liposomal doxorubicine in folate receptor-expressing tumor models," Cancer Chemotherapy and Pharmacology (2010)). Here, as before, folate (e.g., folic acid) is used as the targeting ligand. As discussed in this disclosure, a targeted drug using folic acid as the targeting moiety is biologically no different than a regular untargeted cytotoxic because a drug of such construct binds to both folate receptor alpha and RFCs or PCFTs. Because a targeted liposome with a large payload of a cytotoxic drug is likely being delivered to a normal cell when the targeting moiety is a folate, such as folic acid, this therapy is likely to seriously exacerbate toxicity. In fact, Zalipsky et al. observed that toxic deaths were aggravated in cases where a folate depleted diet existed.

It is important to overcome the main pharmacological challenges associated with treatment with gemcitabine. This goal could be achieved by exploiting for example a cancer specific morphology, which has been unappreciated as useful to the goal of targeting FR-α: the loss of polarity by tumor tissue cells.

Disruption of cell polarity and tissue disorganization is a hallmark of advanced epithelial tumors. As illustrated in FIG. 1A, normal simple epithelium generally comprises a monolayer of individual cells that display a distinct apical-basal polarity. Cells are tightly packed and connected to each other by the apical junctional complexes (FIG. 1A-101), which separate apical and basolateral membrane domains. In normal tissue where polarity is preserved, folate receptor alpha is attached at the apical surface of cells situated away from, and out of direct contact with folates in the blood circulation (FIG. 1A-102). FIG. 1B illustrates how cells in high-grade epithelial tumors display loss of apical-basal polarity and overall tissue disorganization, putting folate receptor alpha in direct contact with folates in the blood circulation (1B-103). This feature of tumor tissue cells, was believed by the inventors to have greater significance for antifolate based therapies than conventional thinking had appreciated. The belief was that this held a significant potential to rehabilitate antimetabolites as anticancer therapies while minimizing associated severe and sometime life-threatening toxicities.

One of our goals is to design a chemical entity to deliver gemcitabine with or without one or more additional agents selected from (1) platinum, (2) platinum derivative, (3) taxane, (4) taxane derivative, (5) camptothecin, and (6) camptothecin derivative, in a manner that selectively targets specifically FR-α while avoiding RFCs, one can limit exposure of antimetabolites to tumor tissue cells only, because these tumor tissue cells overexpress folate receptor alpha while this receptor is concurrently in direct contact with blood circulation, which is not the case for normal tissues where FR-α is expressed. One further goal is to extend the utility of the chemical entity and methods to other cell surface folate receptors because of their structural and functional similarities to FR-α.

It is increasingly becoming recognized that therapeutic strategies that include enhancing the immune system to selectively target cancer cells and enhance cancer immunosurveillance (cancer vaccination) can be very effective in the treatment of cancer. Unfortunately, current approaches involving cytotoxic therapy do not take this into consideration. More often than not cytotoxic therapy results in a diminished capacity for the patient's immune system to fight cancer and, in some cases, frank antagonism whereby the patient's immune system protects cancer cells. Because of this, there is a need to develop therapeutic strategies that harness an optimal cytotoxic effect of chemotherapy with an increased ability for the patient's immune system to fight cancer.

New Chemical Entity

Described herein, among other things, is a targeted PEGylated liposomal gemcitabine (PLG) composition, comprising a PEGylated liposome including entrapped and/or encapsulated gemcitabine; and a targeting moiety comprising an amino acid chain, the amino acid chain comprising a plurality of amino acids, the targeting moiety having a specific affinity for at least one type of folate receptor, the targeting moiety attached to one or both of a PEG and an exterior of the liposome. Specific affinity may, for example, include an equilibrium dissociation constant (Kd) in a range of $0.5 \times 10^{-10}$ to $10 \times 10^{-6}$ moles [0.05 nanoMole to 10 μMole] for at least one type of folate receptor.

The contemplated new chemical entity is an antibody drug conjugated (ADC) folate receptor-targeted liposomal gemcitabine (LG) with or without one or more additional agents selected from (1) platinum, (2) platinum derivative, (3) taxane, (4) taxane derivative, (5) camptothecin, and (6) camptothecin derivative. The one or more additional agents could bring a potentially safe and more effective gemcitabine based treatment to a large number of patients with FR-α-positive cancer. The main limitation of non-liposomal gemcitabine use is its rapid disintegration by cytidine deaminase and clearance in vivo. The new chemical entity shields gemcitabine from breakdown into its inactive form by cytidine deaminase found in patient plasma, or produced in tumor microenvironment by TAMs, or associated with hypoxic tumor microenvironment. It preferentially targets tumor cells for exposure to gemcitabine with or without one of the additional agents and reduces and/or minimizes exposure of such gemcitabine based drug cocktail to normal cells, especially the high turnover normal cells in the bone marrow and in the epithelial lining of the gastrointestinal tract. Finally, the new chemical entity has the ability to transport gemcitabine with or without the one or more additional agent across cell membrane into a tumor cell in a manner that is primarily independent from gemcitabine cross-cell membrane human nucleoside transporters such as hENT1.

The new molecular (chemical) entity may further include a hapten. The hapten or antigen or a combination thereof are there to facilitate the immune system clearing of the diseased cells by providing immune-enhancing and immune-activating functions and by enhancing a patient's immunosurveillance during treatment or after treatment. The new chemical entity is especially relevant in the treatment of patients with advanced stage of disease that may be immunocompromised. These immunological effects are mediated by various humoral and cellular immune cells such as mast cells, B-cells, T-cells, NKT cell, phagocytes, macrophages, neutrophils, cytotoxic T-cells etc.

Preferred haptens include, but are not limited to, fluorescein (FITC) or Beta 1, 6-glucan.

The rationale for FITC is that, in addition to being an imaging agent, FITC has been shown to elicit the property of a hapten (Lu et al.: Preclinical Pharmacokinetics, Tissue Distribution, and Antitumor Activity of a Folate-Hapten Conjugate-Targeted Immunotherapy in Hapten-immunized Mice. Mol. Cancer Ther. (2006); 5(12) 3258-3267), incorporated by reference herein in its entirety.

Beta 1, 6-glucan is a naturally occurring glucose polymer found on the cell wall of fungi. The rationale for the choice of Beta 1, 6-glucan as a preferred hapten stems from several observations (Bejerano et al. Phagocytosis by Human Neutrophils Is Stimulated by a Unique Fungal Cell Wall Component. Cell Host Microbe, 2007; 2(1):55-67): (1) innate immunity depends on the recognition of surface features common to a broad portfolio of pathogens; (2) the cell wall of fungi evokes a powerful immunostimulatory response; (3) the glucose polymer Beta has been implicated in fungal immune recognition; (4) among Beta 1, 3-glucan and Beta 1, 6-glucan, the two kinds of Beta-glucans found in fungal walls, the minor cell wall Beta 1, 6-glucan mediate neutrophils activity more efficiently than Beta 1, 3-glucan, as measured by engulfment, production of reactive oxygen species (ROS's) and expression of heat shock proteins; (5) neutrophils rapidly ingest beads coated with Beta 1,6-glucan while ignoring those coated with Beta 1, 3-glucan; (6) complement factors C3b/C3d are deposited on Beta 1, 6-glucan more readily than on Beta 1, 3-glucan; and (7) Beta 1, 6-glucan has also been found to be important for efficient engulfment of the human pathogen Candida albicans.

The successful application of gemcitabine based treatment in ovarian, lung, pancreas and breast cancer makes a compelling argument for development and use of a folate receptor-targeted nanoparticle containing gemcitabine alone or with the one or more additional agents selected from (1) platinum, (2) platinum derivative, (3) taxane, (4) taxane derivative, (5) camptothecin, and (6) camptothecin derivative, because these tumors express FR-α. Despite substantial improvements in treatment with newly approved therapies, pancreatic cancer, lung cancer, breast cancer and ovarian cancer remain a serious and life-threatening disease requiring new safe and more effective therapeutic options. Some 70% or more of ovarian cancers overexpress FR-α while the other tumor types express FR-α with varying degrees. Invariably, the vast majority of solid tumors express FR-α with much higher degrees as the disease progresses to advanced stage.

Available preclinical and clinical data suggest that a folate receptor-targeted nanoparticle containing gemcitabine alone or with a platinum agent like cisplatin or a taxane like paclitaxel could be effective in this setting. In addition, there are many tumor types in which gemcitabine is effective or approved. The use of gemcitabine-based regimen in these tumor types has been limited because of toxicity. Concurrently many of these tumors also express FR-α by way of loss of cell polarity, particularly in advanced disease settings. Hence, a strategy to develop a safer gemcitabine targeting FR-α positive tumors stands to benefit a large number of patients with different tumor types that express FR-α. These patients represent a highly unmet medical need. To address this need, the present disclosure proposes a class of new chemical entities designed as tumor cell specific folate receptor-targeted liposomal gemcitabine that spare normal cells, while at the same time overcome the pharmacological challenges of gemcitabine based therapy and delivering a more effective payload of gemcitabine or other nucleoside analogs to the cancer cells.

According to various example embodiments, the liposomes contained in the liposome composition of the examples can also be targeting liposomes, e.g., liposomes including one or more targeting moieties or biodistribution modifiers on the surface of the liposomes. Example embodiments of targeting liposomes may, for example, be called immunoliposomes. A targeting moiety can be any agent that is capable of specifically binding or interacting with a desired target. In an example embodiment, a targeting moiety may be a moiety that binds with specificity and affinity to a folate receptor, such as, for example, folate receptor alpha, folate receptor beta and/or folate receptor delta. Such binding may be directed towards the ligand (e.g., folate) binding site of the folate receptor or may be directed to a part of the folate receptor that does not directly bind the ligand—that is, directed to an epitope of the folate receptor other than the ligand binding site. Folate receptors are distinct and different from reduced folate carriers and exploit different pathways to the interior of the cells. The targeting moiety, according to example embodiments, specifically and preferentially binds to and/or internalizes into, a target cell in which the liposome-entrapped entity exerts its desired effect. A target cell may, for example, be a cancer cell, a tumor cell and/or a metastatic cell. In an example embodiment, the liposome carrying a targeting moiety is internalized by a target cell.

In any of the example embodiments of this disclosure, the targeting moiety may be a protein which an antigen binding sequence of an antibody. It is understood that when the protein refers to an antibody, it may be a single chain amino acid (e.g., single chain antibody) or an antibody comprising two or more chains of amino acids, such as the traditional antibody comprising a heavy chain and a light chain. In an example embodiment, the protein may, for example, have a three-dimensional structure of, at least, the antigen binding site of an antibody. One example of such a protein as a targeting moiety is an antibody. However a complete antibody is not necessary. For example, a protein that is a targeting moiety of any of the example embodiments may comprise one or more complementary determining regions (CDRs) of antibody origin. More specifically, the protein that is a targeting moiety may comprise all 6 CDRs of an antibody comprising a heavy and light chain. Examples of suitable proteins that can serve as targeting moieties include at least one selected from the group consisting of an antibody, a humanized antibody, an antigen binding fragment of an antibody, a single chain antibody, a single-domain antibody, a bi-specific antibody, a synthetic antibody, a pegylated antibody and a multimeric antibody. An antibody may have a combination of these characteristics. For example, a humanized antibody may be an antigen binding fragment and may be pegylated and multimerized as well. Antibodies to folate receptor alpha are commercially available.

An example of antibody that may be employed is a murine antibody against folate receptor alpha. The sequence is described in U.S. Pat. No. 5,646,253. For example, based on the sequences disclosed, the gene was synthesized and placed into a transient expression vector and the antibody was produced in HEK-293 transient expression system. The antibody can be a complete antibody, a Fab, or any of the various antibody variations discussed.

Affinity is a measure of the strength of interaction between an epitope and an antibody's antigen binding site. It is defined by:

$$K_A = \frac{[Ab - Ag]}{[Ab][Ag]}$$

where $K_A$=affinity constant
[Ab]=molar concentration of unoccupied binding sites on the antibody
[Ag]=molar concentration of unoccupied binding sites on the antigen
[Ab-Ag]=molar concentration of the antibody-antigen complex The affinity of targeting moieties and monoclonal antibodies can be measured accurately by one of ordinary skill in the art. Polyclonal antibodies are heterogeneous antibodies and will contain a mixture of antibodies of different affinities recognizing several epitopes. However, even in this situation an average affinity can be determined by one of ordinary skill in the art. In this disclosure, where a single affinity for targeting moiety cannot be determined, the affinity is defined as an average affinity. Specific affinity as used herein is described above.

Each of the liposomes may comprise any number of targeting moieties, such as, for example, and without limitation, from 30 to 250 targeting moieties, such as, for example, from 30-200 targeting moieties. Alternatively, each of the liposomes may comprise less than 220 targeting moieties such as, for example, less than 200 moieties. The targeting moieties can be attached, such as, for example, by being covalently bonded to the outside of the liposome. The molecules that are on the outside of the liposome may, for example, comprise, at least, a lipid, a steric stabilizer, a maleimide, a cholesterol and the like. In an example embodiment, the targeting moiety may be covalently bound via a maleimide functional group to at least one selected from the group consisting of a liposomal component and a steric stabilizer such as a PEG molecule. It is possible that all the targeting moieties are bound to one type of component such as PEG. It is also possible that the targeting moieties are bound to different components. For example, some targeting moieties may be bound to the lipid components or cholesterol, some targeting moieties may be bound to the steric stabilizer (e.g., PEG) and still other targeting moieties may be bound to a detectable marker or to another targeting moiety.

In an example embodiment, the targeting moiety has affinity and specificity for at least one or more antigen where the antigen is selected from the group consisting of folate receptor alpha, folate receptor beta, and folate receptor delta. In an example embodiment, the targeting moiety has specific affinity (e.g., affinity and specificity) for at least two antigens selected from the group consisting of folate receptor alpha, folate receptor beta, and folate receptor delta. In another example embodiment, the targeting moiety has specific affinity for three antigens which are, for example, folate receptor alpha; folate receptor beta; and folate receptor delta. The targeting moiety may have affinity and specificity to an epitope of the antigen because sometimes a targeting moiety does not bind the complete antigen but just an epitope of many epitopes in an antigen. In an example embodiment, the targeting moiety has specific affinity for an epitope on a tumor cell surface antigen that is present on a tumor cell but absent or inaccessible on a non-tumor cell. For example, in some situations, the tumor antigen may be on the surface of both normal cells and malignant cancer cells, but the tumor epitope may only be exposed in a cancer cell. As a further example, a tumor antigen may experience a conformation change in cancer causing cancer cell specific epitopes to be present. A targeting moiety with specific affinity to epitopes described in this disclosure are useful and envisioned in the example embodiments. In these embodiments, the tumor cell with cancer cell specific epitopes may be a cancer cell. Examples of such tumor cell surface antigens include, at least, folate receptor alpha, folate receptor beta and folate receptor delta.

Example embodiments relate to a liposomal gemcitabine composition comprising: a medium comprising a liposome including an interior space; gemcitabine disposed within said interior space; a targeting moiety comprising a protein with specific affinity for at least one folate receptor, said targeting moiety disposed at an the exterior of the liposome. In the example embodiments, the medium is an aqueous solution. In an example embodiment, the interior space, the exterior space (e.g., the medium), or both the interior space and the medium contains one or more lyoprotectants or cryoprotectants. In an example embodiment, the cryoprotectants mannitol, trehalose, sorbitol, and sucrose are preferred.

In another example embodiment, the disclosure is based on the discovery that a neutral or anionic liposome (i.e., a non-cationic liposome, a liposome that is not cationic) with affinity and specificity to a folate receptor or more than one folate receptor containing gemcitabine is surprisingly effective against cells presenting and expressing folate receptors on their cell surface.

In an example embodiment, the targeted liposomal gemcitabine is targeted only to one epitope. For example, if the targeted liposomal gemcitabine comprises an antibody, the antibodies may be monospecific to one epitope only. In an embodiment, all of the targeting moieties are specific to a single epitope only. For example, all of the targeting moieties may be the same. That is, they may all be the same antibody. In another preferred embodiment, the one epitope is an epitope in folate receptor alpha, folate receptor beta, or folate receptor delta. In another preferred embodiment, the epitope is not part of the ligand (folate) binding site of folate receptor alpha, folate receptor beta, or folate receptor delta.

As discussed above, the liposomes of example embodiments may comprise a steric stabilizer that can increase their longevity in circulation. The basic concept is that one or more steric stabilizers such as a hydrophilic polymer (Polyethylene glycol (PEG)), a glycolipid (monosialoganglioside (GM1)) or others occupies the space immediately adjacent to the liposome surface and exclude other macromolecules from this space. Consequently, access and binding of blood plasma opsonins to the liposome surface are hindered, and thus interactions of macrophages with such liposomes, or any other clearing mechanism, are inhibited and longevity of the liposome in circulation is enhanced.

For any of the example embodiments which incorporate a steric stabilizer, the steric stabilizer may be at least one from the group consisting of polyethylene glycol (PEG), poly-L-lysine (PLL), monosialoganglioside (GM1), poly(vinyl pyrrolidone) (PVP), poly(acrylamide) (PAA), poly(2-methyl-2-oxazoline), poly(2-ethyl-2-oxazoline), phosphatidyl polyglycerol, poly[N-(2-hydroxypropyl) methacrylamide], amphiphilic poly-N-vinylpyrrolidones, L-amino-acid-based polymer, and polyvinyl alcohol. In example embodiments, the steric stabilizer or the population of steric stabilizer is PEG. In an example embodiment, the steric stabilizer is a PEG with a number average molecular weight (Mn) of 200 to 5000 daltons. These PEGs can be of any structure such as linear, branched, star or comb structure and are commercially available.

According to example embodiments, the liposome composition may be provided as a pharmaceutical composition containing the example liposome composition of the example embodiments and a carrier, e.g., pharmaceutically acceptable carrier. Examples of pharmaceutically acceptable carries are normal saline, isotonic dextrose, isotonic sucrose, Ringer's solution, and Hanks' solution. A buffer substance can be added to provide pH optimal for storage stability. For example, pH between about 6.0 and about 7.5, more preferably pH about 6.5, is optimal for the stability of liposome membrane lipids, and provides for excellent retention of the entrapped entities. Histidine, hydroxyethylpiperazine-ethyl-sulfonate (HEPES), morpholipoethylsulfonate (MES), succinate, tartrate, and citrate, typically at 2-20 mM concentration, are exemplary buffer substances. Other suitable carriers include, e.g., water, buffered aqueous solution, 0.4% NaCl, 0.3% glycine, and the like. Protein, carbohydrate, or polymeric stabilizers and tonicity adjusters can be added, e.g., gelatin, albumin, dextran, or polyvinylpyrrolidone. The tonicity of the composition can be adjusted to the physiological level of 0.25-0.35 mol/kg with glucose or a more inert compound, such as lactose, sucrose, mannitol, or dextrin. These compositions may be sterilized by conventional, well known sterilization techniques, e.g., by filtration. The resulting aqueous solutions may be packaged for use or filtered under aseptic conditions and lyophilized, the lyophilized preparation being combined with a sterile aqueous medium prior to administration.

The pharmaceutical liposome compositions can also contain other pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the liposome suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable.

The concentration of the liposomes of example embodiments in the fluid pharmaceutical formulations can vary widely, i.e., from less than about 0.05% usually or at least about 2-10% to as much as 30 to 50% by weight and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, liposome pharmaceutical compositions composed of irritating lipids may be diluted to low concentrations to lessen inflammation at the site of administration.

Example embodiments relate to a method of delivering gemcitabine, to a tumor expressing folate receptor on its surface. An example method comprises the step of administering at least one of any of the compositions comprising a liposome in this disclosure in an amount to deliver a therapeutically effective dose of gemcitabine to the tumor.

The amount of liposome pharmaceutical composition administered will depend upon the particular therapeutic entity entrapped inside the liposomes, the disease state being treated, the type of liposomes being used, and the judgment of the clinician. Generally, the amount of liposome pharmaceutical composition administered will be sufficient to deliver a therapeutically effective dose of the particular therapeutic entity.

The quantity of liposome pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). Handbook of Anticancer Drug Development, LWW, 2003. Therapeutically effective dosages for various therapeutic entities are well known to those of skill in the art; and, according to the example embodiments a therapeutic entity delivered via the pharmaceutical liposome composition and provides at least the same or higher activity than the activity obtained by administering the same amount of the therapeutic entity in its routine non-liposome formulation. Typically, the dosages for the liposome pharmaceutical composition of the example embodiments may, for example, range between about 0.005 and about 500 mg of the therapeutic entity per kilogram of body weight, and, most often, between about 0.1 and about 100 mg therapeutic entity/kg of body weight.

An effective amount is a dosage of the agent (e.g., gemcitabine, platinum based drug, taxane based drug, or combinations thereof) sufficient to provide a medically desirable result. The effective amount will vary with the desired outcome, the particular condition being treated or prevented, the age and physical condition of the subject being treated, the severity of the condition, the duration of the treatment, the nature of the concurrent or combination therapy (if any), the specific route of administration and like factors within the knowledge and expertise of the health practitioner. It is preferred generally that a maximum dose be used, that is, the highest safe dose according to sound medical judgment.

For example, if the subject has a tumor, an effective amount may be that amount that reduces the tumor volume or load (as for example determined by imaging the tumor). Effective amounts may also be assessed by the presence and/or frequency of cancer cells in the blood or other body fluid or tissue (e.g., a biopsy). If the tumor is impacting the normal functioning of a tissue or organ, then the effective amount may be assessed by measuring the normal functioning of the tissue or organ. In some instances the effective amount is the amount required to lessen or eliminate one or more and preferably all, symptoms.

The example embodiments provide pharmaceutical compositions. Pharmaceutical compositions are sterile compositions that comprise a sample liposome and preferably gemcitabine preferably in a pharmaceutically-acceptable carrier.

The term "pharmaceutically-acceptable carrier" may, for example, refer to one or more compatible solid or liquid filler, diluents or encapsulating substances that are suitable for administration to a human or other subject contemplated by the example embodiments.

The term "carrier" may refer, for example, to an organic or inorganic ingredient, natural or synthetic, with which liposome compositions are combined to facilitate administration. The components of the pharmaceutical compositions are comingled in a manner that precludes interaction that would substantially impair their desired pharmaceutical efficiency. Suitable buffering agents include acetic acid and a salt (1-2% W/V); citric acid and a salt (1-3% WN); boric acid and a salt (0.5-2.5% W/V); and phosphoric acid and a salt (0.8-2% W/V). Suitable preservatives include benzalkonium chloride (0.003-0.03% WN); chlorobutanol (0.3-0.9% W/V); and parabens (0.01-0.25% W/V).

Unless otherwise stated herein, a variety of administration routes are available. The particular mode selected will depend, of course, upon the particular active agent selected, the particular condition being treated and the dosage required for therapeutic efficacy. The methods provided, generally speaking, may be practiced using any mode of administration that is medically acceptable, meaning any mode that produces effective levels of a desired response without causing clinically unacceptable adverse effects. Possible administration routes include injections, by parenteral routes, such as intramuscular, subcutaneous, intravenous, intraarterial, intraperitoneal, intraarticular, intraepidural, intrathecal, intravenous, intramuscular, intra sternal injection or infusion, or others, as well as oral, nasal, mucosal, sublingual, intratracheal, ophthalmic, rectal, vaginal, ocular, topical, transdermal, pulmonary, and inhalation.

In an example embodiment, the liposome pharmaceutical composition may, for example, be prepared as an infusion composition, an injection composition, a parenteral composition, or a topical composition, either as a liquid solution or suspension. However, solid forms suitable for solution in, or suspension in, liquid vehicles prior to injection may also be prepared. The composition may, for example, also be formulated into an enteric-coated tablet or gel capsule according to known methods in the art.

For the delivery of liposomal drugs formulated according to example embodiments, to tumors of the central nervous system, a slow, sustained intracranial infusion of the liposomes directly into the tumor (a convection-enhanced delivery, or CED) may be of particular advantage. See Saito, et al., Cancer Research, vol. 64, p. 2572-2579, 2004; Mamot, et al., J. Neuro-Oncology, vol. 68, p. 1-9, 2004. The compositions may, for example, also be directly applied to tissue surfaces. Sustained release, pH dependent release, or other specific chemical or environmental condition mediated release administration is also specifically included in the example embodiments, e.g., by such means as depot injections, or erodible implants. A few specific examples are listed below for illustration.

For oral administration, the compounds may, for example, be formulated readily by combining the liposomal compositions with pharmaceutically acceptable carriers well known in the art. Such carriers enable formulation as tablets, pills, dragees, capsules, liquids, gels, syrups, slurries, films, suspensions and the like, for oral ingestion by a subject to be treated. Suitable excipients may, for example, include fillers such as sugars, including lactose, sucrose, mannitol, or sorbitol; cellulose preparations, such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). Optionally, the oral formulations may also be formulated in saline or buffers for neutralizing internal acid conditions or may be administered without any carriers.

Pharmaceutical preparations that can be used orally include push-fit capsules made of gelatin, as well as soft, sealed capsules made of gelatin and a plasticizer, such as glycerol or sorbitol. The push-fit capsules can contain the liposomal composition suspended in suitable liquids, such as aqueous solutions, buffered solutions, fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in a conventional manner.

For administration by inhalation, the compositions may be conveniently delivered in the form of an aerosol spray presentation from pressurized packs or a nebulizer, with the use of a suitable propellant, e.g., dichlorodifluoromethane, trichlorofluoromethane, ichlorotetrafluoroethane, carbon dioxide or other suitable gas. In the case of a pressurized aerosol, the dosage unit may be determined by providing a valve to deliver a metered amount.

When it is desirable to deliver the compositions systemically, they may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances that increase the viscosity of the suspension, such as sodium carboxymethyl cellulose, sorbitol, or dextran. Alternatively, suspensions of liposomes may be prepared as oil-based suspensions. Suitable lipophilic solvents or vehicles include fatty oils, such as sesame oil, or synthetic fatty acid esters, such as ethyl oleate or triglycerides.

Alternatively, the liposomal compositions may be in powder form or lyophilized form for constitution with a suitable vehicle, e.g., sterile pyrogen-free water, before use.

The compositions may also be formulated in rectal or vaginal compositions such as suppositories or retention enemas, e.g., containing conventional suppository bases such as cocoa butter or other glycerides.

The example embodiments contemplate administration of agents to subjects having or at risk of developing a cancer, including for example a solid tumor cancer, using the compositions and liposomes of example embodiments. In an example embodiment, the cancer may, for example, be distinguished by the expression of folate receptors on its cell surface. The folate receptor may, for example, include folate receptor alpha, folate receptor beta or folate receptor delta. The example embodiments contemplate that the compositions are able to deliver higher quantities of the gemcitabine, alone or in combination, to these subjects without excessive delivery to normal cells (i.e., cells not expressing folate receptors).

Any cancers that express folate receptors may be treated. It should be noted that some cancers may express folate receptors in an early stage while the majority of cancers may express folate receptors at late stages. The cancer may be carcinoma, sarcoma or melanoma. Carcinomas include, without limitation, to basal cell carcinoma, biliary tract cancer, bladder cancer, breast cancer, cervical cancer, choriocarcinoma, CNS cancer, colon and rectum cancer, kidney or renal cell cancer, larynx cancer, liver cancer, small cell lung cancer, non-small cell lung cancer (NSCLC, including adenocarcinoma, giant (or oat) cell carcinoma, and squamous cell carcinoma), mesothelioma, oral cavity cancer, ovarian cancer, pancreatic cancer, prostate cancer, skin cancer (including basal cell cancer and squamous cell cancer), stomach cancer, testicular cancer, thyroid cancer, uterine cancer, rectal cancer, cancer of the respiratory system, and cancer of the urinary system.

Sarcomas are mesenchymal neoplasms that arise in bone (osteosarcomas) and soft tissues (fibrosarcomas). Sarcomas include, without limitation, liposarcomas (including myxoid liposarcomas and pleiomorphic liposarcomas), leiomyosarcomas, rhabdomyosarcomas, malignant peripheral nerve sheath tumors (also called malignant schwannomas, neurofibrosarcomas, or neurogenic sarcomas), Ewing's tumors (including Ewing's sarcoma of bone, extraskeletal (i.e., not bone) Ewing's sarcoma, and primitive neuroectodermal tumor), synovial sarcoma, angiosarcomas, hemangiosarcomas, lymphangiosarcomas, Kaposi's sarcoma, hemangioendothelioma, desmoid tumor (also called aggressive fibromatosis), dermatofibrosarcoma protuberans (DFSP), malignant fibrous histiocytoma (MFH), hemangiopericytoma, malignant mesenchymoma, alveolar soft-part sarcoma, epithelioid sarcoma, clear cell sarcoma, desmoplastic small cell tumor, gastrointestinal stromal tumor (GIST), and chondrosarcoma.

Melanomas are tumors arising from the melanocytic system of the skin and other organs. Examples of melanoma include, without limitation, lentigomaligna melanoma, superficial spreading melanoma, nodular melanoma, and acral lentiginous melanoma.

The cancer may be a solid tumor lymphoma. Examples include Hodgkin's lymphoma, Non-Hodgkin's lymphoma, and B cell lymphoma.

The cancer may be, without limitation, bone cancer, brain cancer, breast cancer, colorectal cancer, connective tissue cancer, cancer of the digestive system, endometrial cancer, esophageal cancer, eye cancer, cancer of the head and neck, gastric cancer, intra-epithelial neoplasm, melanoma neuroblastoma, Non-Hodgkin's lymphoma, non-small cell lung cancer, small cell lung cancer, mesothelioma, prostate cancer, retinoblastoma, or rhabdomyosarcoma.

The example embodiments may be practiced in any subject that is likely to benefit from delivery of agents as contemplated herein. Human subjects are preferred subjects in example embodiments, but subjects may also include animals such as household pets (e.g., dogs, cats, rabbits, ferrets, etc.), livestock or farm animals (e.g., cows, pigs, sheep, chickens and other poultry), horses, such as thoroughbred horses, laboratory animals (e.g., mice, rats, rabbits, etc.), mammal and the like. Subjects also include fish and other aquatic species.

The subjects to whom the agents are delivered may be normal subjects. Alternatively, they may have or may be at risk of developing a condition that can be diagnosed or that can benefit from delivery of one or more particular agents. In an example embodiment, such conditions include cancer (e.g., solid tumor cancers or non-solid cancer, such as leukemias). In a more preferred embodiment, these conditions include cancers involving cells that express folate receptors on their cell surface.

Tests for diagnosing the conditions embraced by the example embodiments are known in the art and will be familiar to the ordinary medical practitioner. The determination of whether a cell type expresses folate receptors can be made using commercially available antibodies. These laboratory tests include, without limitation, microscopic analyses, cultivation dependent tests (such as cultures), and nucleic acid detection tests. These include wet mounts, stain-enhanced microscopy, immune microscopy (e.g., FISH), hybridization microscopy, particle agglutination, enzyme-linked immunosorbent assays, urine screening tests, DNA probe hybridization, serologic tests, etc. The medical practitioner will generally also take a full history and conduct a complete physical examination in addition to running the laboratory tests listed above.

A subject having a cancer may, for example, be a subject that has detectable cancer cells. A subject at risk of developing a cancer may, for example, be a subject that has a higher than normal probability of developing cancer. These subjects include, for instance, subjects having a genetic abnormality that has been demonstrated to be associated with a higher likelihood of developing a cancer, subjects having a familial disposition to cancer, subjects exposed to cancer causing agents (i.e., carcinogens), such as tobacco, asbestos, or other chemical toxins, and subjects previously treated for cancer and in apparent remission.

In an example embodiment, the methods may selectively deliver a liposomal gemcitabine composition to the tumor at a rate which is higher, e.g., at least two-fold greater, than a cell not expressing folate receptor.

Example embodiments relate to a method of making any of the compositions of this disclosure. In an example embodiment, the method involves forming a mixture comprising: (1) liposomal components; (2) gemcitabine in aqueous solution; and (3) the targeting moiety. The mixture may then be homogenized to form liposomes in said aqueous solution. Further, the mixture may be extruded through a membrane to form liposomes enclosing the gemcitabine in an aqueous solution. It is understood the liposomal components comprise any lipid (including cholesterol) of this disclosure, including functionalized lipids and lipids attached to targeting moieties, detectable labels, and steric stabilizers, or any subset of all of these. It is further noted that the gemcitabine in aqueous solution may comprise any reagents and chemicals discussed for the interior or exterior of the liposome including, for example, buffers, salts, cryoprotectants and the like.

The method may further comprise the optional step of lyophilizing the composition after said removing step to form a lyophilized composition. As stated above, the gemcitabine in aqueous solution may comprise cryoprotectants which may be any cryoprotectants, are listed in this disclosure. If the composition is to be lyophilized, a cryoprotectant may be preferred.

Further, after the lyophilizing step, the method can comprise the optional step of reconstituting said lyophilized composition by dissolving the lyophilized composition in a solvent after said lyophilizing step. Methods of reconstitution are well known. One preferred solvent is water. Other preferred solvents include saline solutions and buffered solutions.

While certain example embodiments are discussed, it should be understood that liposomes can be made by any method that is known or will become known in the art. See, for example, G. Gregoriadis (editor), Liposome Technology, vol. 1-3, 1st edition, 1983; 2nd edition, 1993, CRC Press, Boca Raton, Fla. Examples of methods suitable for making liposome composition include extrusion, reverse phase evaporation, sonication, solvent (e.g., ethanol) injection, microfluidization, detergent dialysis, ether injection, and dehydration/rehydration. The size of liposomes can be controlled by controlling the pore size of membranes used for low pressure extrusions or the pressure and number of passes utilized in microfluidisation or any other suitable methods.

In general, the gemcitabine is contained inside, that is, in the inner (interior) space of the liposomes. In an example embodiment, the gemcitabine that is not encapsulated in the liposome is partially or substantially completely removed from the outer medium surrounding the liposomes. Such removal can be accomplished by any suitable means known to one skilled in the art, e.g., dilution, ion exchange chromatography, size exclusion chromatography, dialysis, ultrafiltration, precipitation, etc. Therefore, one optional step may comprise a step of: removing gemcitabine in aqueous solution outside of the liposomes after said extruding step.

Another example embodiment relates to a targeted liposomal composition that selectively targets folate receptors comprising: a liposome including an interior space, gemcitabine disposed within said interior space, a steric stabilizer molecule attached to an exterior of the liposome, and a targeting moiety comprising a protein with specific affinity for at least one folate receptor, said targeting moiety attached to at least one of the steric stabilizer and the exterior of the liposome.

The example embodiments further contemplate in vitro applications of the compositions and methods. In vitro use may be, for example, in the use such as cell culturing and tissue engineering where selective treatment of a subpopulation of cells are desired. For example, during the culture of stem cells from a normal patient or a patient suffering from cancer, the cells can be treated with a sample composition or sample liposome as discussed to address cancerous subpopulations of cells. The cancerous subpopulation may arise because the donor originally has cancer or because the cells spontaneously transform during in vitro procedures.

According to example embodiments, the liposomes and liposome compositions can be provided in a kit comprising a container with the liposomes, and optionally, a container with the entity and an instruction, e.g., procedures or information related to using the liposome composition in one or more applications. Such instruction can be provided via any medium, e.g., hard paper copy, electronic medium, or access to a database or website containing the instruction.

Inter alia, this disclosure provides improvements to the efficacy and safety of delivering gemcitabine to cancer cells by providing a targeted PEGylated liposomal gemcitabine (PLG). The disclosure also contemplates providing a PLG with or without a platinum or a taxane. The disclosure provides improvements to, for example, U.S. Patent Application Publication No. US2008/0213183 and the work described in Federico et al., 2012: "Gemcitabine-loaded Liposomes: Rationale, Potentialities and Future Perspectives", Internal Journal of Nanomedicine, Vol. 2012; 7: 5423-5436, and Immordino et al. 2004: "Preparation, characterization, cytotoxicity and pharmacokinetics of liposomes containing lipophilic gemcitabine prodrugs," Journal of Controlled Release, 100 (2004): 331-346, the entire contents of which are incorporated by reference herein in their entireties. The contents of WO 2016/025882 are also incorporated herein in their entirety.

While the above technology has been described in connection with what is presently considered to be the most practical and preferred embodiments, it is to be understood that the technology is not to be limited to the disclosed embodiment, but on the contrary, is intended to cover various modifications and equivalent arrangements included within the spirit and scope of the appended claims.

EXAMPLES

The following examples are intended to illustrate but not to limit the disclosure in any manner, shape, or form, either explicitly or implicitly. While they are typical of those that might be used, other procedures, methodologies, or techniques known to those skilled in the art may alternatively be used. The example compositions comprise example liposomes. Both example composition and example liposome are used in the experiments described in the examples section and throughout this disclosure are specific embodiments of the disclosure and are not meant to define the full scope of the disclosure.

Example 1: Production of Folate Receptor Alpha Targeted Liposomes Containing Gemcitabine and a Hapten Production of Gemcitabine Liposomes Gemcitabine is encapsulated in liposomes by the following procedure. First, the lipid components of the liposome membrane are weighed out and combined as a concentrated solution in ethanol at a temperature of around 65° C. In this example, the lipids used are hydrogenated soy phosphitidyl choline, cholesterol, DSPE-PEG-2000 (1,2-distearoyl-sn-glycero-3-phosphoethanolamine-N-[methoxy(polyethylene glycol)-), PEG-DSPE-malemide and PEG-DSPE-FITC. The molar ratio of HSPC: Cholesterol: PEG-DSPE is approximately 3:2:0.15. Next, gemcitabine is dissolved in an aqueous buffer at a starting concentration of 25 mg/ml. The drug solution is heated to 65° C. The ethanolic lipid solution is injected into the gemcitabine solution using a small bore needle. During this step the drug solution is well stirred using a magnetic stirrer. The mixing is performed at an elevated temperature (63° C. -72° C.) to ensure that the lipids are in the liquid crystalline state (as opposed to the gel state that they attain at temperatures below the lipid transition temperature Tm=51° C. -54° C.). As a result, the lipids are hydrated and form multiple bilayer (multilamellar) vesicles (MLV) containing gemcitabine in the aqueous core.

Downsizing of MLV's Using Filter Extrusion

The MLVs are fragmented into unilamellar (single bilayer) vesicles of the desired size by high-pressure extrusion using three passes through stacked (track-etched polycarbonate) membranes. The membranes used during the first pass have a pore size of 200 nm. The membranes used during the second pass have a pore size of 100 nm as the final pass. During extrusion, the temperature is maintained above the Tm to ensure plasticity of the lipid membranes. As a result of the extrusion, large and heterogeneous in size and lamellarity MLVs turn into small, homogenous (80-100 nm) unilamellar vesicles (ULV) that sequester the drug in their interior. A Malvern Zetasizer Nano ZS instrument (Southborough, MA) with back scattering detector(90°) was used for measuring the hydrodynamic size (diameter) at 25° C. in a quartz micro cuvette. The samples were diluted 50-fold in formulation matrix before analysis.

Our results show that liposomes down sized using filter extrusion had an average particle size of 118 nM with a PDI of 0.017 and a zeta potential of −12.4. As an alternative to filter extrusion, high pressure microfluidization can also be used to down size liposomes. We have been able to produce liposomes having a size from 40 nm and up, such as between 30-150 nm (data not shown) or even smaller than 30 nm, and particularly between 40 nm and 120 nm using methods such as high pressure filter extrusion or microfluidization alone or in combination.

Tangential Flow Filtration (TFF) and Drug Formulation

After the ULV's containing gemcitabine have been produced, the extra-liposomal gemcitabine is removed using dialysis or tangential flow diafiltration against a suitable buffer. Although any buffer solution can be used, in this example the buffer used was Hepes Buffered Saline, pH 6.5. Upon completion of dialysis, filter sterilize was performed using a 0.22 micron filter.

Thiolation of Anti-Folate Receptor Alpha Antibody

In order to conjugate the antibody (in this case the anti-folate receptor antibody) to the PEG-DSPE-malemide moieties on the liposome, the antibody needs to be thiolated. In this example, thiolation of the antibody is achieved using Traut's reagent (Themo Fisher Scientific). The antibody is added to freshly prepared 14 mM Trauts reagent and 5 mM EDTA in phosphate buffered saline at a pH of 8.1. After incubation with gentle stirring for 60 minutes, the thiolated antibody is separated from excess Trauts reagent by dialysis against 200 volumes of 25 mM HEPES pH 7.0, 60 mM NaCl for a minimum of 4 hours.

Conjugation of Thiolated Antibody to the Gemcitabine Liposomes

The amount of thiolated antibody to be used is calculated based on the desired number of antibodies per liposomes. A 2-fold excess of each preparation of thiolated antibody is added to diafiltered sterile liposomes. The reaction vessel is overlaid with nitrogen gas and incubated overnight with slow stirring at room temperature of 4° C. The conjugation reaction is stopped by blocking unreacted maleimide groups by adding a stock aqueous 100 mM L-Cysteine-HCl solution to a final concentration of 15 mM in the reaction mixture. Free thiolated antibody is then separated from the antibody conjugated liposomes by using size exclusion chromatography.

Example 2: Cell Lines Used for Experiments

Cells lines used in the experiments are commercially available from sources such as the ATCC (American Type Culture Collection of Manassas, Virginia, U.S.A). The cell lines, their ATCC accession numbers and growth conditions are listed below.

- NCI-H2452 (ATCC® CRL-5946TH); RPMI-1640 (Cat. #30-2001); 10% HI FBS; 1% Pen/Strep; 1% L-Glutamine.
- PANC-1 (ATCC® CRL-1469TH); Dulbecco's Modified Eagle's Medium (DMEM) (ATCC® 30-2002TM) 10% HI FBS; 1% Pen/Strep; 1% L-Glutamine
- SKBR3; McCoy 5A Medium; 10% HI FBS; 1% Pen/Strep; 1% L-Glutamine.
- HPAF-II ATCC CRL-1997; Eagle's Minimum Essential Medium (EMEM) (ATCC® 30-2003Tm)); 10% HI FBS; 1% Pen/Strep; 1% L-Glutamine.

Example 3 MTS Assay

Cancer cell lines were seeded in 96 well plates on day 0 at optimal cell numbers. On day 1, drug formulations were added at 2-fold serial dilutions. The cells were incubated for 3-5 days and the level of inhibition of cellular proliferation was measured by the MTS assay (3-(4,5-dimethylthiazol-2-yl)-5-(3-carboxymethoxyphenyl)-2-(4-sulfophenyl)-2H-tetrazolium assay). The commercially available MTS Cell Proliferation Assay Kit (Colorimetric) (197010) is a colorimetric sensitive quantification of viable cells in proliferation and cytotoxicity assay. The assay is based on the reduction of MTS tetrazolium compound by viable cells to generate a colored formazan product that is soluble in cell culture media.

The MTS experiments are performed as follows: The night before, the cells are seeded according to the amount of cells required for each cell line in 96 well tissue culture plate. Final volume in each well is 100 μL (see Table of cell lines for reference; all cell lines obtained from ATCC).

The seeded cells are incubated at 37° C. and 5% CO 2 overnight. The next day, the drugs were prepared in the cell-specific cell culture media and added to the cells.

On day 4, the effect on cellular proliferation was measured with MTS assay. 10 μl of reagent (Celltiter 96® Aqueous One Solution) were added to each well. This is a colormetric assay that turns deep purple when there is extensive cellular proliferation. The plates were incubated for 2 hours at 37° C. and the absorbance was measured at 490 nm. Percent inhibition of cell growth was calculated using the untreated cell absorbance values set at 100% for each cell line.

Example 4 Effect on Cellular Proliferation

Liposomes were targeted with a monoclonal antibody specific for hFOLR1. Cells were grown in 96 well plates for 4 days in presence of no drug Gemcitabine or Targeted Liposomal Gemcitabine. Values indicate IC50 of each formulation.

FIG. 2 shows the effect of gemcitabine on NCI-2452 mesothelioma cancer cells (see, FIG. 2A) compared to Targeted Liposomal Gemcitabine on the same cells (see, FIG. 2B). While gemcitabine has an $IC_{50}$ of 30.39, Targeted Liposomal Gemcitabine has an $IC_{50}$ of 2.292. This indicates that a lower dose of Gemcitabine is required to inhibit growth of NCI-H2452 mesothelioma cancer cells when formulated within a targeted liposome (B) compared to Gemcitabine alone (A).

FIG. 3 shows the effect of gemcitabine on PANC-1 pancreatic cancer cells (see FIG. 3A) compared to Targeted Liposomal Gemcitabine on the same cells (see, FIG. 3B). While gemcitabine has an $IC_{50}$ of 11.02, Targeted Liposomal Gemcitabine has an $IC_{50}$ of 2.522. This indicates that, a lower dose of Gemcitabine is required to inhibit growth of PANC-1 pancreatic cancer cells when formulated within a targeted liposome (B) compared to Gemcitabine alone (A).

FIG. 4 shows the effect of gemcitabine on SKBR3 breast cancer cells (see FIG. 4A) compared to Targeted Liposomal Gemcitabine on the same cells (see, FIG. 4B). While gemcitabine has an $IC_{50}$ of 296.9, Targeted Liposomal Gemcitabine has an $IC_{50}$ of 0.4459. This indicates that, a lower dose of Gemcitabine is required to inhibit growth of PANC-1 pancreatic cancer cells when formulated within a targeted liposome (B) compared to Gemcitabine alone (A).

FIG. 5 shows the effect of gemcitabine on HPAF-II pancreatic cancer cells (see FIG. 5A) compared to Targeted Liposomal Gemcitabine on the same cells (see, FIG. 5B). While gemcitabine has an $IC_{50}$ of 9.109, Targeted Liposomal Gemcitabine has an $IC_{50}$ of 0.9501. This indicates that, a lower dose of Gemcitabine is required to inhibit growth of PANC-1 pancreatic cancer cells when formulated within a targeted liposome (B) compared to Gemcitabine alone (A).

Figure 7:
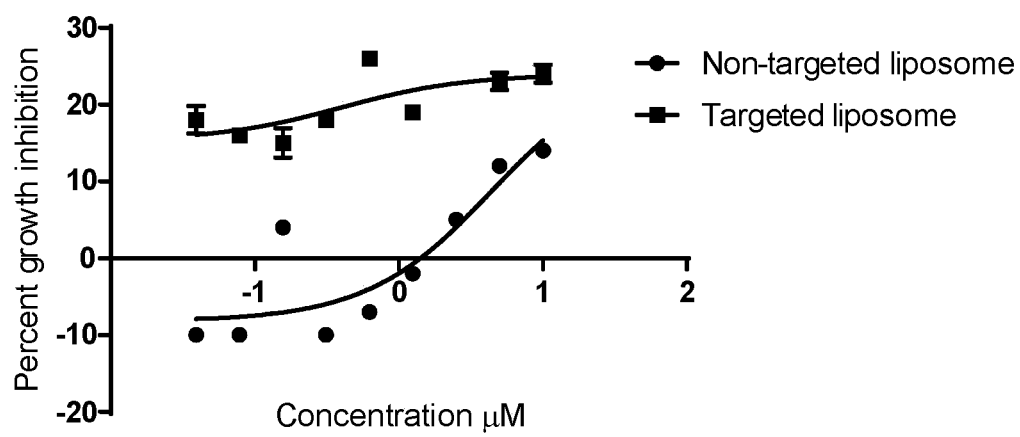
FIG. 7 depicts (1) percent growth inhibition of Targeted Liposomal Gemcitabine on NCIH2452 lung (mesothelioma) cancer cells (top line) and (2) percent growth inhibition of Non-Targeted Liposomal Gemcitabine on NCIH2452 lung cancer cells (bottom line).

FIG. 7 shows the effect of non-Targeted Liposomal Gemcitabine on NCI-2452 lung cancer cells (see FIG. 7 top line) compared to Targeted Liposomal Gemcitabine on the same cells (see, FIG. 7 bottom line). While non-Targeted Liposomal Gemcitabine has an $IC_{50}$ of 4.441, Targeted Liposomal Gemcitabine has an 1050 of 0.4045. This indicates that a lower dose of Gemcitabine is required to inhibit growth of NCI-H2452 lung cancer cells when formulated within a targeted liposome (B) compared to non-targeted liposomal gemcitabine alone (A). This is significant in showing that Targeted Liposomal Gemcitabine is significantly more effective than non-Targeted Liposomal Gemcitabine.

Composite data demonstrating that Targeted Liposomal Gemcitabine has a significantly lower $IC_{50}$ on multiple types of cancer cell lines when compared to free Gemcitabine. Our results, in terms of $IC_{50}$s (μM), is summarized as follows:

| Cells | Free Gemcitabine | Targeted Liposomal Gemcitabine |
|---|---|---|
| SKBR3 breast cancer | 296.9 | 0.4459 |
| NCI-H2452 lung cancer | 30.39 | 2.292 |
| PANC-1 pancreatic cancer | 11.02 | 2.522 |
| HPAF-II pancreatic cancer | 9.109 | 0.9501 |

Example 5 Determining Folate Receptor Expression on NCI-H2454 Cells

The level of folate receptor alpha on the cell surface of NCI-H2454 cells was measured by flow cytometry with a monoclonal antibody conjugated with a fluorochrome. A shift to the right after binding of an antibody (see, FIG. 6) compared to the line before antibody treatment (see, FIG. 6) indicates the detection of receptor by flow cytometry. The more the histogram shifts to the right relative to the untreated cells the higher the levels of receptors are on the cell surface. FIG. 6 shows that 27% of the cells exhibit high levels of folate receptor alpha on cancer cells, but almost undetectable levels on normal cells. This example is provided as an example of a cancer cell line (NCI-H2452) with relatively increased levels of folate receptor alpha on the cell surface. As previously shown in U.S. Published Patent Application No. 2016/0228573 (Application Ser. No. 14/826,967, filed Aug. 14, 2015 and claiming priority to provisional Application Ser. No. 62/037,597 filed Aug. 14, 2014 each incorporated herein by reference) uptake of folate receptor targeted antibody drug conjugates is driven by cell surface expression of folate receptor alpha in addition to dose. The impact of targeting (as opposed to not targeting) with an antibody directed against folate receptor alpha is shown in the results previously described for FIG. 7.

In these experiments, the assays were performed as follows:

Cell were collected and washed in 0.2% Bovine serum albumin in PBS (FACS buffer.) Cell were resuspended in 100 μl volume in FACS buffer. 5 μl of anti-folate receptor alpha monoclonal conjugated with APC was added (cat #FAB5646A; R&D Systems). The cells were incubated for 30 min in the dark at 4° C. 100 μl of FACS buffer was added to wash the cells and then the cells were evaluated by flow cytometry.

Example 6 Sample Liposome Reduces The Toxicity Of Gemcitabine On Bone Marrow-Derived Neutrophils.

The level of a molecule called CD15 is elevated on more mature neutrophils. This molecule is elevated on cells in the circles drawn on the plots.

FIG. 8. Neutrophil differentiation assay. One of the major side effects from gemcitabine treatment is the reduction of neutrophils in the bloodstream that counter infections. This is the result of CD34+ stem cells not differentiating, or developing, into mature neutrophils in the bone marrow. We measured the effect of targeted liposomal gemcitabine on neutrophil differentiation compared to the same dose of gemcitabine (10 and 50 μM.) Hematopoietic progenitor cells (CD34+) were purchased and treated with a panel of growth factors to induce neutrophil differentiation. CD34+ cells that were also treated with gemcitabine failed to develop into mature neutrophils.

CD34+ stem cells were cultured without (A) or with (B) cytokines (growth factors) that induce neutrophil differentiation in vitro, including stem cell factor, IL-3, and GM-CSF for 2 days. This process resulted in some CD34+ cells being induced to differentiate into neutrophils using growth factors. By day 2, there is a dramatic increase in mature neutrophils depicted in the oval. Compare FIG. 8A where the cells did not receive growth factors with FIG. 8B. The cells within the drawn gate (FIG. 8B) are larger, more complex maturing neutrophils that are lacking in in FIG. 8A.

FIG. 9. Gemcitabine inhibits neutrophil differentiation in vitro. CD34+ stem cells were cultured with cytokines and growth factors that induce neutrophil differentiation in vitro (stem cell factor, IL-3, and GM-CSF) with or without Gemcitabine for 2 days. In the presence of growth factors with 50 µM gemcitabine (FIG. 9A) and in the presence of growth factors with 10 µM gemcitabine (FIG. 9B) neutrophil differentiation is inhibited when compared to cells in FIG. 8B.

FIG. 10. Targeted Liposomal Gemcitabine preserves some neutrophil differentiation. CD34+ stem cells were cultured with cytokines and growth factors that induce neutrophil differentiation in vitro (stem cell factor, IL-3, and GM-CSF) with or without Targeted Liposomal Gemcitabine. In the presence of growth factors with 50 µM Targeted Liposomal Gemcitabine (FIG. 10A) and growth factors with 10 µM Targeted Liposomal Gemcitabine (FIG. 10B) neutrophil differentiation is much less inhibited and significant amount of neutrophils are seen.

Taken together, these results clearly show that a higher number of neutrophils were able to differentiate in the presence of 50 µM or 10 µM Targeted Liposomal Gemcitabine in contrast to cells grown in the presence of growth factors and free gemcitabine (See FIGS. 8B, 9A & 9B).

In more detail, experiments were performed as follows: CD34+ stem cells were obtained from ATCC. CD34+ cells were thawed at 37° C. for 1 minute. While on ice, the cells were transferred to cold stem cell medium ("StemSpan SFEM"—Stem Cell Tech. cat. #9650), 10% heat activated fetal bovine serum (HI FBS.) Each vial contained approximated $5\times10^5$ cell/ml. The cells were placed in 96 well tissue culture plates 35,000 cell/well.

The neutrophils GROWTH media contained 100 ng/ml of stem cell factor human (SCF-Sigma H8416, lot #MKBT8036V), 20 ng/ml of granulocyte colony-stimulation factor, human (G-CSF-Sigma H5541, lot #SLBC9602V), 10 ng/ml of IL3 recombinant human (Sigma SRP3090, lot #1008AFC13) in StemSpam media as above.

The cells were also treated as follows 1) StemSpam media alone with no growth cytokines; 2) StemSpam media+ growth cytokines, and 3) Gemcitabine, Targeted Liposomal Gemcitabine and non-Targeted Liposomal Gemcitabine in amounts as indicated.

Cells were incubated for 1-5 days and assayed at each time point for mature neutrophils by flow cytometry with antibodies to CD15, Mac-1, and CD34. The cells shown in the circle on the plots are maturing neutrophils expressing Mac-1 and CD34.

Targeted Liposomal Gemcitabine preserves neutrophil differentiation compared to Gemcitabine alone. The data is summarized in FIG. 11, which shows the reduction of toxicity on bone marrow production of neutrophils. In FIG. 11, panel A, the population of live cells within the neutrophil gate at day 2 is shown. Briefly, all the tests take place with cytokines (growth factors) except for the experiment represented by the leftmost column. In the leftmost column, the media is not supplemented with cytokines and the proportion of live cell is low at 5% or less. When the media was supplemented with cytokines, the percentage of live cells exceeds 60%. In contrast, in the presence of gemcitabine 50 µM or 10 µM, the percentage of live cells were less than 20% or less than 5%. In contrast, Targeted Liposomal Gemcitabine at 50 µM and 10 µM shows better survival of neutrophils.

FIG. 11, Panel B, shows a series of similar experiments showing the reduction of toxicity on bone marrow production of maturing neutrophils—specifically CD15+ neutrophils. Briefly, all the tests take place with cytokines except for the experiment represented by the leftmost column. In the leftmost column, the media is not supplemented with cytokines and the number of life cells is less than 300. When the media was supplemented with cytokines, the number of live cells exceed 6000. In contrast, in the presence of gemcitabine 50 µM or 10 µM, the number of live cells were less than 100. In contrast, Targeted Liposomal Gemcitabine at 50 µM and 101.1M shows better survival of neutrophils with the number of live cells around 300 to 1000. In short higher numbers of neutrophils were able to differentiate in the presence of 50 µM or 10 µM Targeted Liposomal Gemcitabine and growth factors when compared to neutrophils grown in the presence of 501.1M or 10 µM 'Free' Gemcitabine and growth factors.

Although the disclosure has been described with reference to various example embodiments, it should be understood that various modifications can be made without departing from the spirit of the disclosure. Accordingly, the scope of the disclosure should be determined with reference to the appended claims, along with the full scope of equivalents to which such claims are entitled. The disclosures of all cited articles and references, including patent applications and publications, are incorporated herein by reference for all purposes.

What is claimed is:

1. A method of delivering gemcitabine to a tumor expressing a folate receptor on its surface, the method comprising the step of: administering a pharmaceutical composition comprising a targeted PEGylated liposomal gemcitabine (PLG) in an amount to deliver a therapeutically effective dose of the gemcitabine to the tumor, wherein the targeted PLG comprises: a unilamellar anionic PEGylated liposome encapsulating one or more agents, wherein the PEGylated liposome has a diameter in the range 80 nm to 130 nm wherein the one or more agents comprises gemcitabine and Beta 1, 6-glucan; wherein the PLG comprises one or more targeting moiety comprising an antibody, a fragment of an antibody or a component of an antibody having a specific affinity for at least one type of folate receptor, the one or more targeting moiety conjugated to one or more maleimide moieties attached to-one or both of a PEG and an exterior of the liposome.

2. The method of claim 1, wherein the tumor is in a patient and the administering is selected from the group consisting of: infusion; injection; parenteral administration; topical administration; intraperitoneal injection; direct intratumor injection; intra-arterial injection; intravenous injection; subcutaneous injection; intramuscular injection; transcutaneous delivery; and intranasal delivery.

3. The method of claim 2, wherein the patient is a human.

4. The method of claim 2, wherein the patient is a non-human mammal.

5. The method of claim 1, wherein the PEGylated liposome further comprises one or more of an immunostimulatory agent, a detectable marker and a maleimide moiety disposed on at least one of the PEG and the exterior of the liposome.

6. The method of claim 1, wherein the targeted PLG comprises a targeting moiety having an equilibrium dissociation constant (Kd) between $0.5 \times 10^{-10}$ to $10 \times 10^{-6}$ moles for at least one type of folate receptor.

7. The method of claim 1, wherein the targeted PLG comprises at least one targeting moiety having specific affinity for one or more selected from the group consisting of folate receptor alpha, folate receptor beta and folate receptor delta.

8. The method of claim 1, wherein the targeted PLG comprises one or more targeting moiety selected from the group consisting of: an antibody, a humanized antibody, an antigen binding fragment of an antibody, a single chain antibody, a single-domain antibody, a mono-specific antibody, a bi-specific antibody, a synthetic antibody, a pegylated antibody, and a multimeric antibody.

9. The method of claim 1, wherein the PLG does not contain encapsulated cytidine deaminase.

10. The method of claim 9, wherein the cytidine deaminase is one or more of the enzymes that converts gemcitabine and other nucleotide analogues into inactive forms in patient plasma, produced in tumor microenvironment by tumor associated macrophages (TAMs), and/or associated with hypoxic tumor microenvironment.

11. The method of claim 1, wherein the targeted PLG further comprises one or more agents selected from the group consisting of: platinum; platinum derivative; taxane; taxane derivative; camptothecin; and a camptothecin derivative.

12. A method for treating cancer in a patient comprising administering to the patient an effective amount of a pharmaceutical composition comprising a targeted PEGylated liposome encapsulating gemcitabine and Beta 1, 6-glucan, wherein the exterior of the liposome comprises one or more targeting moiety comprising an antibody, a fragment of an antibody or a component of an antibody having a specific affinity for at least one type of folate receptor (PLG).

13. The method of claim 12 wherein the cancer is a tumor.

14. The method of claim 13 wherein the tumor expresses a folate receptor.

15. The method of claim 13 wherein the method inhibits or reduces tumor cell proliferation.

16. The method of claim 12 wherein the cancer is one or more selected from the group consisting of: pancreatic cancer; breast cancer; ovarian cancer; bladder cancer; lung cancer; prostate cancer; head cancer; neck cancer; gastric cancer; gastrointestinal cancer; colon cancer; esophageal cancer; cervical cancer; kidney cancer; biliary duct cancer; gallbladder; hematologic malignancy; leukemia; lymphoma; and mesothelioma.

17. The method of claim 12, wherein the patient is a human.

18. The method of claim 12, wherein the patient is a non-human mammal.

19. The method of claim 12, wherein the targeted PEGylated liposome PbG comprises a targeting moiety having an equilibrium dissociation constant (Kd) between $0.5 \times 10^{-1}$ to $10 \times 10^{-6}$ moles for at least one type of folate receptor.

20. The method of claim 12, wherein the targeted PEGylated liposome comprises at least one targeting moiety having specific affinity for one or more selected from the group consisting of folate receptor alpha, folate receptor beta and folate receptor delta.

21. The method of claim 12, wherein the targeted PEGylated liposome comprises one or more targeting moiety selected from the group consisting of: an antibody, a humanized antibody, an antigen binding fragment of an antibody, a single chain antibody, a single-domain antibody, a mono-specific antibody, a bi-specific antibody, a synthetic antibody, a pegylated antibody, and a multimeric antibody.

22. The method of claim 12, wherein the targeted PEGylated liposome does not contain encapsulated cytidine deaminase.

23. The method of claim 22, wherein the cytidine deaminase is one or more of the enzymes that converts gemcitabine and other nucleotide analogues into inactive forms in patient plasma, produced in tumor microenvironment by tumor associated macrophages (TAMs), and/or associated with hypoxic tumor microenvironment.

24. The method of claim 12, wherein the targeted PEGylated liposome further comprises one or more agents selected from the group consisting of: platinum; platinum derivative; taxane; taxane derivative; camptothecin; and a camptothecin derivative.

* * * * *